(12) United States Patent
Bisanz et al.

(10) Patent No.: US 10,487,305 B2
(45) Date of Patent: Nov. 26, 2019

(54) FOOD GRADE BACTERIA FOR THE REMOVAL OF TOXIC COMPOUNDS

(71) Applicants: LONDON HEALTH SCIENCES CENTRE RESEARCH INC., London (CA); COMPAGNIE GERVAIS DANONE, Paris (FR)

(72) Inventors: Jordan Bisanz, St. Thomas (CA); Gregor Reid, Komoka (CA); Marc Monachese, Oakville (CA); Johan Van Hylckama Vlieg, Marly le Roi (FR); Tamara Smokvina, Orsay (FR); Jeremy Burton, London (CA)

(73) Assignees: LONDON HEALTH SCIENCES CENTRE RESEARCH INC., London (CA); COMPAGNIE GERVAIS DANONE, Paris (FR)

( * ) Notice: Subject to any disclaimer, the term of this patent is extended or adjusted under 35 U.S.C. 154(b) by 0 days.

(21) Appl. No.: 14/390,685

(22) PCT Filed: Apr. 5, 2013

(86) PCT No.: PCT/CA2013/000328
§ 371 (c)(1),
(2) Date: Oct. 3, 2014

(87) PCT Pub. No.: WO2013/149333
PCT Pub. Date: Oct. 10, 2013

(65) Prior Publication Data
US 2015/0191691 A1 Jul. 9, 2015

Related U.S. Application Data

(60) Provisional application No. 61/620,796, filed on Apr. 5, 2012.

(51) Int. Cl.
| | | |
|---|---|---|
| C12N 1/20 | (2006.01) |
| A62D 3/02 | (2007.01) |
| A61K 35/747 | (2015.01) |
| C12R 1/225 | (2006.01) |
| A23C 9/123 | (2006.01) |
| C12N 15/74 | (2006.01) |
| A61K 35/74 | (2015.01) |
| C12N 15/10 | (2006.01) |
| A61K 38/00 | (2006.01) |
| C12N 15/70 | (2006.01) |
| C12N 15/86 | (2006.01) |
| A23K 20/00 | (2016.01) |
| A23K 20/10 | (2016.01) |
| A23K 10/18 | (2016.01) |

(52) U.S. Cl.
CPC ............. *C12N 1/20* (2013.01); *A23C 9/1234* (2013.01); *A61K 35/747* (2013.01); *A62D 3/02* (2013.01); *C12N 15/746* (2013.01); *C12R 1/225* (2013.01); *A23K 10/18* (2016.05); *A23K 20/00* (2016.05); *A23K 20/10* (2016.05); *A23Y 2220/73* (2013.01); *A61K 35/74* (2013.01); *A61K 38/00* (2013.01); *C12N 15/102* (2013.01); *C12N 15/70* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 5,531,988 A | 7/1996 | Paul et al. | |
| 6,080,401 A | 6/2000 | Reddy et al. | |
| 6,479,051 B1 * | 11/2002 | Bruce | A61K 35/745 424/93.45 |
| 6,641,808 B1 | 11/2003 | Bojrab et al. | |
| 2009/0029447 A1 * | 1/2009 | Squire | A62D 3/02 435/262.5 |
| 2009/0035288 A1 * | 2/2009 | Albers | A23C 9/12 424/93.45 |

FOREIGN PATENT DOCUMENTS

WO WO 2011150098 * 12/2011

OTHER PUBLICATIONS

Wilson, Lawrence, "Toxic metals and Detoxification", http://drlwilson.com/articles/TOXIC%20METALS.htm, 2015, pp. 1-60.*
Brudnak, M.A., "Probiotics as an adjuvant to detoxification protocols", Medical Hypotheses, 2002, 58(5), pp. 382-385.*
Mahaffey, Kathryn R., "Mercury Exposure: Medical and Public Health Issues", Transactions of the American Clinical and Climatological Association, 2005, vol. 116, pp. 127-154.*
Kajander et al., "Effects of multispecies probiotic supplementation on intestinal microbiota in irritable bowel syndrome", Alimentary Pharmacology & Therapeutics, 2007, vol. 26, pp. 463-473.*
Assefa et al.," Lactobacilli with probiotic potential in the prairie vole (*Microtus ochrogaster*)" , Gut Pathog., 2015, 7:35, pp. 1-16.*
LFA, www.lifefitnessacademy.com/2008/11/22/probiotics-and-mercury/ , pp. 1-5.*
Saxelin, Maija, "Probiotic Formulations and Applications, the Current Probiotics Market, and Changes in the Marketplace: A European Perspective", Clinical Infectious Diseases, 2008, vol. 46, pp. S76-79.*
Raloff, Janet, "Probiotics: better off dead?", Science & the Public, https:// www.sciencenews.org/blog/science-public/probiotics-better-dead , Publsihed Aug. 26, 2009, pp. 1-2.*
Kiyono et al., "Genetic Engineering of Bacteria for Environmental Remediation of Mercury", Journal of Health Science, 2006, vol. 52, No. 3, pp. 199-204.*
ATSDR, Agency for Toxic Substances and Disease Registry, Public Health Statement Mercury, CAS# 7439-97-6, published Mar. 1999, pp. 1-20.*
Gratz et al., "Lactobacillus rhamnosus strain GG modulates intestinal absorption, fecal excretion, and toxicity of aflatoxin B1 in rats", Applied and Environmental Microbiology, 2006, vol. 72, No. 11, pp. 7398-7400.*

(Continued)

*Primary Examiner* — Laura Schuberg
(74) *Attorney, Agent, or Firm* — Eduardo Krupnik

(57) ABSTRACT

The present invention relates to food-grade bacteria and methods for removing toxic compounds, including lead, cadmium, mercury, arsenic and pesticides, from contaminated environments or substances.

13 Claims, 17 Drawing Sheets

(56) References Cited

OTHER PUBLICATIONS

Hakansson et al., "Gut Microbiota and Inflammation", Nutrients, 2011, vol. 3, pp. 637-682 (Year: 2011).*

Fuchs, S. et al, Detoxifcation of patulin and ochratoxin A, two abundant mycotoxins, by lactic acid bacteria, Food and Chemical Toxicology, 2008, p. 1398-1407, vol. 46, Elsevier Ltd.

Hermandez-Mendoza, A. et al, Screening of Lactobacillus casei strains for their ability to bind aflatoxin B1, Food and Chemical Toxicology, 2009, p. 1064-1068, vol. 47, Elsevier Ltd.

Ndagijimana, M. et al, Effect of a synbiotic food consumption on human gut metabolic profiles evaluated by 1H Nuclear magnetic Resonance spectroscopy, International Journal of Food Microbiology, 2009, p. 147-153, vol. 134, Elsevier Ltd.

Rajkumar, M. et al, Potential of siderophore-producing bacteria for improving heavy metal phytoextraction, Trends in Biotechnology, 2009, p. 142-149, vol. 28, No. 3, Elsevier Ltd.

Sharp, D., Environmental Toxins, a potential risk factor for Diabetes among Canadian Aboriginals, International Journal of Circumpolar Health, 2009, p. 316-326, vol. 68, No. 4.

Singh, J.S. et al, Genetically engineered bacteria: An emerging tool for environmental remediation and future research perspectives, Gene, 2011, p. 1-9, vol. 480, Elsevier Ltd.

Ibrahim, F. et al, Probiotic bacteria as potential detoxification tools: assessing their heavy metal binding isotherms, Can. J. Microbiol, 2006, p. 877-885, vol. 52.

Bhakta, J.N. et al, Isolation and probiotic characterization of arsenic-resistant lactic acid bacteria for uptaking arsenic, World Academy of Science, Engineering and Technology, 2010, vol. 47.

Salim, A.B. et al, Effect of lactic acid bacteria against heavy metals toxicity in rats, J. American Sci., 2011, p. 264-274, vol. 7, No. 4.

Halttunen, T. et al, Rapid removal of lead and cadmium from water by lactic acid bacteria, Int. J. Food Microbiol., 2007, p. 30-35, vol. 114.

Halttunen, T. et al, Arsenic removal by native and chemically modified lactic acid bacteria, Int. J. Food Microbiol., 2007, p. 173-178, vol. 120.

Pierides, M. et al, Ability of dairy strains of lactic acid bacteria to bind aflatoxin M1 in a food model, J. Food Protection, 2000, p. 645-650, vol. 63, No. 5.

Haskard, C. et al, Factors affecting the sequestration of aflatoxin by Lactobacillius rhammosus strain GG, Chemico-Biological Interactions, 2000, p. 39-49, vol. 128.

El-Nezami, H., et al, Ability of Lactobacillus and Proprionibacterium strains to remove aflatoxin B1 from chicken duodenum, J. Food Protection, 2000, p. 549-552, vol. 63, No. 4.

Sambrook, J., et al, Molecular Cloning: A laboratory manual, 1989, 2nd Edition, Chapter 15, Cold Spring Harbor Laboratory Press.

* cited by examiner

A.

B.

FOOD GRADE BACTERIA FOR THE REMOVAL OF TOXIC COMPOUNDS

CROSS REFERENCE TO RELATED APPLICATIONS

This application is a national stage application under 35 U.S.C. 371 of International Application No. PCT/CA2013/000328, filed 5 Apr. 2013, which in turn claims the benefit under 35 U.S.C. 119(e) of U.S. Provisional Ser. No. 61/620,796, filed Apr. 5, 2012, the contents of each of which are hereby incorporated by reference into the present disclosure.

FIELD OF THE INVENTION

The present invention relates to food grade bacteria for improving detoxification. More particularly, the present invention relates to food grade bacteria, or extracts thereof, and to methods of using food grade bacteria or extracts thereof to reduce uptake of ingested toxic compounds and to methods of sequestering toxic compounds from the environment to which the food-grade bacteria is exposed to.

BACKGROUND OF THE INVENTION

Humans and animals in general, are exposed to many toxic compounds that contaminate the environment, food chain, water supply and various items that are part of everyday life. These range in number, type and exposure from ingredients in toothpaste and shampoos to drugs and pathogens in well-water. Amongst Canadian First Nation and Inuit populations, environmental toxins are risk factors for other highly prevalent diseases, especially type 2 diabetes [Sharp D. Environmental toxins, a potential risk factor for diabetes among Canadian Aboriginals. Int J Circumpolar Health. 2009; 68(4):316-26]. A large over-the-counter consumer market has arisen under the guise of 'detox', but most of the products have no rationale or clinical evidence to support their use. The concept of detox has great appeal to consumers, both the health-conscious and others concerned with the growing number of stories in the media about pollution and diseases related to toxic substances. Thus, there is substantial interest in this area, few effective products and a growing need.

The replenishment or boosting of the beneficial organisms through administration of probiotics has become feasible in Canada relatively recently, and has led to much interest amongst consumer and healthcare professionals. Indeed, probiotics are one of the fastest growing food segments in North America. However, gaining insight into the mechanisms by which indigenous microbes and exogenous probiotics affect the subject has been limited.

Probiotic Lactobacilli and bifidobacteria have been shown to help manage several gut pathologies. For example, U.S. Pat. No. 6,641,808 disclosing the use of Lactobacilli for the treatment of obesity; U.S. Pat. No. 5,531,988, discloses a mixture of an immunoglobulin and a bacterium, such as Lactobacilli or *bifidobacterium* or mixtures thereof, that may be used to treat diarrhea, constipation, and gas/cramps; U.S. Pat. No. 6,080,401 discloses a combination of probiotics having *Lactobacillus acidophilus* and *Bifidobacterium bifidus* and herbal preparations for aiding in weight loss, and so forth.

The ability of probiotic products to ameliorate toxins has been much less studied, but nevertheless has some foundation. For example, Lactobacilli and/or bifidobacteria have been found to alter the subjects intestinal metabolic signature [Ndagijimana, M. Laghi L, Vitali B, Placucci G, Brigidi P, Guerzoni M E. Effect of synbiotic food consumption on human gut metabolic profiles evaluated by 1H nuclear magnetic resonance spectroscopy. Int J Food Microbiol. 2009; 134: 147-153]; bind to aflatoxin (*Lactobacillus* strains) [Hernandez-Mendoza A, Garcia H S, Steele J L. Screening of *Lactobacillus casei* strains for their ability to bind aflatoxin B1. Food Chem Toxicol. 2009; 47(6):1064-8]; and detoxify or bind and negate other mycotoxins (*B. animalis*) [Fuchs S, Sontag G, Stidl R, Ehrlich V, Kundi M, Knasmüller S. Detoxication of patulin and ochratoxin A, two abundant mycotoxins, by lactic acid bacteria. Food Chem Toxicol. 2008; 46(4):1398-407].

In summary, the problem associated with toxic compounds is real, and of growing concern to consumers.

Heavy Metals

Heavy metal toxicity is one of the largest health risks in the 21st century. Consumption of lead and cadmium through environmental exposure and diet has been directly responsible for poor health outcomes including: impaired neurological function and loss of IQ, osteoporosis, lung and kidney cancer.

Heavy metals such as lead and cadmium are present in the natural environment, and therefore many bacteria over time have developed mechanisms of resistance to these metals which generally include actively precipitating and sequestering the metals intra/extra cellular or the active efflux of metals out of the cell cytoplasm. Non-food grade bacteria have been investigated for their use in sequestration and detoxification of heavy metals and have shown success (JS Singh et al. Genetically engineered bacteria: An emerging tool for environmental remediation and future research perspectives. Gene. July 2011. 40 (1-2):1-9); Rajkumar et al. Potential of siderophore-producing bacteria for improving heavy metal phytoextraction. Trends Biotechnol. March 2010. 28 (3):142-149).

Mercury

Mercury is one of the most toxic substances known to man and its consumption by a subject is linked to poor health outcomes including altered neurological development in children. Yet, North Americans and Europeans are estimated to consume 6.7 μg daily of inorganic mercury and methylmercury (World Health Organization, 1991).

Mercury is present in the natural environment, and as such, many bacteria have adopted mechanisms of resistance to it, which generally reduce mercury levels in the surrounding environment. Many non-food grade bacteria have been investigated for their use in sequestration and detoxification of mercury and mercury compounds in the environment, however the application of food grade bacteria has not been demonstrated to date.

Arsenic

Arsenic is a metalloid element which commonly comes in two oxidation states: arsenate (As V) and arsenite (As III). Arsenic is found distributed globally often in the earth's crust, it is highly soluble in water and is found in high concentrations in ground water. Arsenic toxicity has been linked to a number of cases and is known to cause organ failure, cancer and death. Main routes of exposure is through ingestion via diet, often arsenic contaminated waters are used for irrigation of farmland resulting in accumulation of the metal in plants and food.

Pesticides

Pesticides such as malathion and parathion fall into the class of organophosphate compounds and act as cholinesterase inhibitors. Malathion is one of the most widely used pesticides in the U.S., and parathion use has recently been limited and is not used in many developed nations due to high toxicity. However, produce imports still consistently detect levels of parathion on produce and it is used in some rare instances in North America.

Major routes of public exposure is through consumption via diet. Agricultural workers and industrial workers are at increased risk of exposure through work place by absorption or inhalation if safety protocols not properly followed.

In view of the problems associated to the exposure of any of the above toxic compounds, it would be advantageous to provide for food grade bacteria that can sequester toxic compounds, including heavy metals, mercury, arsenic, pesticides, such as malathion and parathion, or a combination thereof, from the gastrointestinal tract of a subject to reduce the amount of the toxic compound available to be absorbed by the subject, while detoxifying the toxic compounds directly reduces the toxicity of toxic compounds available to be absorbed by the subject.

SUMMARY OF THE INVENTION

It is an object of the present invention to provide for food-grade bacteria or extracts thereof for the removal and/or neutralization of toxic products from an environment or from a substance to which the food-grade bacteria is exposed to, that solve the deficiencies inherent in traditional detoxification treatments. The present invention provides methods and uses of food grade bacteria for removal and/or neutralization of toxic products found in the internal environment of animals, in the environment to which the animal is exposed or in substance ingested or to be ingested by the animals that may avoid adverse side effects, is reasonable in cost, and may be beneficial in reducing the risk of diseases related to said toxic products. Further, the present invention is relatively easy to manufacture and deliver to a subject.

It is an object of the present invention to provide for food grade bacteria, or extracts thereof, to detoxify and/or sequester toxic compounds, including heavy metals, mercury, arsenic and pesticides, with the application of reducing a subject's toxic compounds exposure and uptake.

As such, in one embodiment, the present invention provides food-grade bacteria or extracts thereof for removing of toxic compounds from a substance or environment to which the food-grade bacteria is exposed to.

In one embodiment, the present invention provides for a composition comprising a food-grade bacteria and a suitable carrier, whereby the composition comprises an effective dose of the food-grade bacteria to remove a toxic compound from a substance or environment to which the food-grade bacteria is exposed to.

In one embodiment of the composition of the present invention, the therapeutically effective dose is at least about $1 \times 10^9$ of the food-grade bacteria per milliliter or less of the suitable carrier.

In another embodiment of the composition of the present invention, the suitable carrier is a carbohydrate-containing medium.

In another embodiment of the composition of the present invention, the carbohydrate-containing medium is a milk-based product.

In another embodiment of the composition of the present invention, the toxic compound is selected from the group consisting of lead, cadmium, mercury, arsenic, malathion and parathion.

In another embodiment of the composition of the present invention, the food-grade bacteria are provided dead or live.

In another embodiment of the composition of the present invention, the food-grade bacteria are provided as an extract.

In another embodiment of the composition of the present invention, the composition comprises a combination of two or more different species of food-grade bacteria.

In another embodiment of the composition of the present invention, the composition comprises a combination of two or more strains of *Lactobacillus rhamnosus, Lactobacillus casei, Lactobacillus crispatus, Lactobacillus fermentum, Lactobacillus johnsonii, Lactobacillus plantarum, Lactobacillus reuteri,* and *Lactobacillus amylovorus.*

In another embodiment of the composition of the present invention, the food-grade bacteria is selected from the group of food-grade bacteria listed in Table 1 shown below. It is mentioned that a bacteria strain of interest is the *Lactobacillus rhamnosus* strain deposited, according to the Budapest Treaty, at CNCM (Collection Nationale de Cultures de Microorganismes, 25 rue du Docteur Roux, Paris) on Mar. 5, 2013, under the accession number CNCM I-4719. This strain is also referred to as "DN 116-060" or R37.

In another embodiment of the composition of the present invention, the environment is an aqueous environment.

In another embodiment, the present invention is a composition, the composition including food-grade bacteria, a carrier and an animal's feed, wherein the food-grade bacteria is capable of removing a toxic compound from a substance or environment to which the food-grade bacteria is exposed to and the food-grade bacteria comprises a bacterial isolate selected from the group consisting of the food-grade bacteria listed in Table 1 or any combination thereof.

In one embodiment, the present invention is a method for reducing a subject uptake of toxic compounds consumed by the subject, the method including administering to the subject an effective dose of a food-grade bacteria capable of sequestering the toxic compound consumed by the subject.

In another embodiment, a method for removing a toxic compound from a substance or environment which is contaminated or suspected of being contaminated with the toxic compound is provided, the method including contacting the substance or environment with food-grade bacteria capable of removing the toxic compound from the substance or the environment.

In one embodiment, the present invention is a method of reducing the toxic effects of a toxic compound in a subject, the method including: administering to the subject a therapeutically effective amount of a food-grade bacteria capable of removing the toxic compound from a substance or environment.

In one embodiment of the previous methods of the present invention the toxic compound is selected from the group consisting of lead, cadmium, mercury, arsenic, malathion and parathion.

In another embodiment of the previous methods of the present invention the food-grade bacteria are provided dead or live.

In another embodiment of the previous methods of the present invention the food-grade bacteria are provided as an extract.

In another embodiment of the previous methods of the present invention the food-grade bacteria comprise a combination of two or more different species of food-grade bacteria.

In another embodiment of the previous methods of the present invention the composition comprises a combination of two or more strains of *Lactobacillus rhamnosus, Lactobacillus casoi, Lactobacillus crispatus, Lactobacillus fer-*

*mentum, Lactobacillus johnsonii, Lactobacillus plantarum, Lactobacillus reuteri*, and *Lactobacillus amylovorus*

In another embodiment of the previous methods of the present invention the food grade bacteria are selected from the group of food-grade bacteria listed in Table 1.

In one embodiment, the present invention is a method of obtaining a strain of *Lactobacillus* capable of removing a toxic compound from an environment, the method including a step of mutagenesis or genetic transformation of the *Lactobacillus*.

In one embodiment, the present invention is a method for obtaining a cell fraction capable of removing a toxic compound from an environment, including the steps of: a) culturing a *Lactobacillus* strain, and b) recovering the cell fraction from the culture in step a).

In one embodiment of the last two methods the toxic compound is selected from the group consisting of lead, cadmium, mercury, arsenic, malathion and parathion. In another embodiment *Lactobacillus* is provided dead or live. In another embodiment the *Lactobacillus* is provided as an extract. In another embodiment the *Lactobacillus* includes a combination of two or more different strains. In another embodiment, the *Lactobacillus* is selected from the group of Lactobacilli listed in Table 1.

In one embodiment, the present invention is a use of a food grade bacteria for the removal of a toxic compound from a substance or an environment.

In one embodiment of the use of the food grade bacteria, the toxic compound is selected from the group consisting of lead, cadmium, mercury, arsenic, malathion and parathion.

In another embodiment of the use of the food grade bacteria, the food-grade bacteria are provided dead or live.

In another embodiment of the use of the food grade bacteria, the food-grade bacteria are provided as an extract.

In another embodiment of the use of the food grade bacteria, the food grade bacteria are provided as a combination of two or more different species of food-grade bacteria.

In another embodiment of the use of the food grade bacteria, the food grade bacteria are provided as two or more strains of *Lactobacillus rhamnosus, Lactobacillus casei, Lactobacillus crispatus, Lactobacillus fermentum, Lactobacillus johnsonii, Lactobacillus plantarum, Lactobacillus reuteri*, and *Lactobacillus amylovorus*.

In another embodiment of the use of the food grade bacteria, the food-grade bacteria is selected from the group of food-grade bacteria listed in Table 1.

In another embodiment, the present invention provides for a method for removing a toxic compound from a substance which is suspected of being contaminated with said toxic compound comprising contacting the substance with food-grade bacteria or extract thereof capable of removing the toxic compound from the substance.

In another embodiment, the present invention provides for a method of reducing the toxic effects of a toxic compound in a subject, the method comprising: administering to the subject a therapeutically effective amount of food-grade bacteria of Table 1 or any combination thereof.

In one embodiment, the present invention provides for a method of obtaining a strain of *Lactobacillus* capable of removing a toxic compound from an environment, the method includes a step of mutagenesis or genetic transformation of the *Lactobacillus*.

In another embodiment, the present invention is a method for obtaining a cell fraction capable of removing a toxic compound from an environment. The method, in one embodiment, includes the steps of: a) culturing a *Lactobacillus* strain, and b) recovering the cell fraction from the culture in step a).

In one embodiment of the methods of the present invention, the food-grade bacteria comprise a combination of two or more different species of food-grade bacteria.

In one embodiment of the present invention, the food grade bacteria is a *Lactobacillus*.

In one aspect of the present invention the toxic compound includes a heavy metal.

In another aspect of the present invention, the toxic compound includes a heavy metal and the food-grade bacteria comprise dead bacteria.

In another aspect of the present invention, the toxic compound includes a heavy metal and the food-grade bacteria comprise live bacteria.

In one another of the present invention, the toxic compound includes a heavy metal and the food-grade bacteria comprise a mixture of dead bacteria and live bacteria.

In another aspect of the present invention the heavy metal is cadmium.

In another aspect of the present invention the heavy metal is lead.

In another aspect of the present invention the toxic compound includes mercury.

In another aspect of the invention the mercury is inorganic mercury.

In another aspect of the invention the mercury is organic mercury.

In one aspect of the present invention, the toxic compound includes mercury and the food-grade bacteria comprise dead bacteria.

In one aspect of the present invention, the toxic compound includes mercury and the food-grade bacteria comprise live bacteria.

In one aspect of the present invention, the toxic compound includes mercury and the food-grade bacteria comprise a mixture of dead bacteria and live bacteria.

In another aspect of the present invention the toxic compound includes arsenic.

In one aspect of the present invention, the toxic compound includes arsenic and the food-grade bacteria comprise dead bacteria.

In one aspect of the present invention, the toxic compound includes arsenic and the food-grade bacteria comprise live bacteria.

In one aspect of the present invention, the toxic compound includes arsenic and the food-grade bacteria comprise a mixture of dead bacteria and live bacteria.

In another aspect of the present invention the toxic compound includes a pesticide.

In one aspect of the present invention, the toxic compound includes a pesticide and the food-grade bacteria comprise dead bacteria.

In one aspect of the present invention, the toxic compound includes a pesticide and the food-grade bacteria comprise live bacteria.

In one aspect of the present invention, the toxic compound includes a pesticide and the food-grade bacteria comprise a mixture of dead bacteria and live bacteria.

In another aspect of the present invention the pesticide is selected from malathion or parathion.

In another aspect of the present invention, the toxic compound includes endotoxins.

In another aspect of the present invention, the toxic compound includes heterocyclic aromatic amines.

In another aspect of the present invention, the toxic compound includes acrylamide.

BRIEF DESCRIPTION OF THE FIGURES

The present invention will become more fully understood from the detailed description given herein and from the accompanying drawings, which are given by way of illustration only and do not limit the intended scope of the invention.

FIG. 1 B is a graph illustrating the ability of food grade Lactobacilli to remove cadmium (Cd) from a solution (error bars±SEM).

FIG. 2 B is a graph illustrating the ability of food grade Lactobacilli to remove cadmium (Cd) compared to E. coli (error bars±SEM).

FIG. 3 B is a graph illustrating the ability of live and dead food grade Lactobacilli to remove cadmium (Cd) from a solution (error bars±SEM).

FIG. 6 B is a scanning electron micrograph of *Lactobacillus rhamnosus* R37 (top) and a corresponding energy-dispersive X-ray spectrum of a portion of a cell containing visible deposits.

FIG. 9 B is a graph illustrating the growth of a number of Lactobacilli species in MRS media having cadmium.

FIG. 10 B is a graph illustrating the ability of a food grade bacterium of the present invention to remove $Hg^{2+}$ from a solution having a 15 part per billion (ppb) $Hg^{2+}$ inoculum (error bars±SEM; * signifies significant (p<0.05) difference by an unpaired T-test).

DETAILED DESCRIPTION OF THE INVENTION

Definitions

Figure 1:
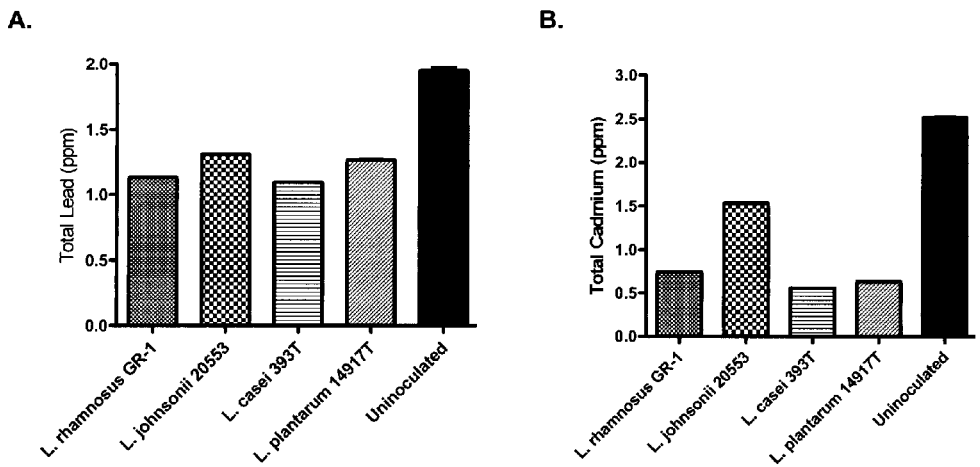
FIG. 1 A is a graph illustrating the ability of food grade Lactobacilli to remove lead (Pb) from a solution (error bars±SEM).

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise.

The expression "food grade bacteria" refers to any bacteria, alive or dead, that have no harmful effect on human health or that have a GRAS (generally recognized as safe) status. Such bacteria maybe selected from the group consisting of Lactobacilli and Bacilli. Non-limiting examples of food-grade bacteria particularly suitable for the purpose of the present invention are listed in Table 1.

The term "probiotic" as used in this document refers to food-grade bacteria which perform beneficial functions to subject organisms when they are present and alive in viable form in the subject organisms.

"Food production animal" is used herein to describe any animal that is prepared and used for human consumption. A food production animal can be, but not limited to, a ruminant animal such as beef and dairy cattle, pigs, lamb, chicken, turkey or any other form, or aquatic animals including shrimp, lobster or fish used for human consumption.

As used herein, the term "removing a toxic compound from a substance or environment" refers to a removal of one or more toxic compounds that can be tested as described in at least one of the examples below.

"Subject" or "subjects" are used herein to describe a member of the animal kingdom, including food production animals and humans.

The present invention also encompasses mutant strains or genetically transformed strains derived from a parent strain. These mutant or genetically transformed strains can be strains wherein one or more endogenous gene(s) of the parent strain has (have) been mutated, for instance to modify some of its metabolic properties (e.g., its ability to ferment sugars, its resistance to acidity, its survival to transport in the gastrointestinal tract, its post-acidification properties or its metabolite production). They can also be strains resulting from the genetic transformation of the parent strain by one or more gene(s) of interest, for instance in order to confer to said genetically transformed strains additional physiological features, or to allow it to express proteins of therapeutic or vaccinal interest that one wishes to administer through said strains. These strains can be obtained from a strain by means of the conventional techniques for random or site-directed mutagenesis and genetic transformation of Lactobacilli, such as those described by Gury et al. (2004) or by Perea Vélez et al., 2007, or by means of the technique known as "genome shuffling" (Patnaik et al., 2002 and Wang et al., 2007).

A subject of the present invention is also cell fractions which can be obtained from a *Lactobacillus* strain. They are in particular DNA preparations or bacterial wall preparations obtained from cultures of said strain. They may also be culture supernatants or fractions of these supernatants. By way of example, cell-free supernatant (CFS) of one *Lactobacillus* strain can be obtained using the method for obtaining a CFS from another *Lactobacillus* strain.

A subject of the present invention is also a method for obtaining a cell fraction, comprising the steps of:
a) culturing a *Lactobacillus* strain, and
b) obtaining and/or recovering the cell fraction from the culture in step a).

In compositions of the invention, said strain can be used in the form of whole bacteria which may be living or dead. Alternatively, said strain can be used in the form of a bacterial lysate or in the form of bacterial fractions; the bacterial fractions suitable for this use can be chosen, for example, by testing their properties on mercury removal from an aqueous environment. Preferably the bacterial cells are present as living, viable cells.

Food-Grade Bacteria for Removing Toxic Compounds

In one embodiment, the present invention relates to food-grade bacterial or extracts thereof, including probiotics, capable of removing or sequestering toxic compounds from an environment to which the food-grade bacteria is exposed to, or from a substance which may have or may be suspected of having the toxic compound. Substances may include edible compositions, such as vegetable-based foods or animal-based foods, and may also include drinkable solutions, including water, milk, syrups, extracts and other beverages. Substances may also include raw agricultural products used to produce foods and drinkable solutions. As such, the present invention relates also to methods of using the food-grade bacteria of the present invention to prevent the uptake of toxic compounds by a subject, or in methods to filter toxic compounds out of substances prior to exposing a subject to said substances. The environment may include an aqueous environment, such as the gastro-intestinal tract of a subject, or the environment in which the subject resides, such as a pond.

The food grade bacteria may be any type of bacteria that may be capable of removing toxic compounds from foods or solutions that may be consumed by a subject, or from ingredients used in the manufacture of said foods or solutions. Table 1 includes food-grade bacteria that may be used with the present invention. In a preferred aspect, the food-grade bacteria may be aerobically, microaerophilically or anaerobically grown and may be selected from the group consisting of the food-grade bacteria of Table 1. Administration of the food-grade bacteria, or extract thereof, to a subject may be accomplished by any method likely to introduce the organisms into the gastro-intestinal tract of the subject. The bacteria can be mixed with a carrier and applied to liquid or solid feed or to drinking water. The carrier material should be non-toxic to the subject. When dealing with live food-grade bacteria, the carrier material should also be non-toxic to the food-grade bacteria. When dealing with live food-grade bacteria the carrier, preferably, may include an ingredient that promotes viability of the bacteria during storage. The food-grade bacteria may also be formulated as an inoculant paste to be directly injected into a subject's mouth. The formulation may include added ingredients to improve palatability, improve shelf-life, impart nutritional benefits, and the like. If a reproducible and measured dose is desired, the food-grade bacteria can be administered by a cannula or syringe. The amount of food-grade bacteria to be administered is governed by factors affecting efficacy. When administered in feed or drinking water the dosage can be spread over a period of days or even weeks. The cumulative effect of lower doses administered over several days may be greater than a single larger dose thereof. One or more strains of food-grade bacteria may be administered together. A combination of strains may be advantageous because individual subjects may differ as to the strain which is most persistent in a given individual.

The present invention is also directed to extracts or fragments of food-grade bacterial that may be capable of removing or sequestering toxic compounds from a substance or sample. As shown herein, the inventors found that dead food-grade bacteria may be used to sequester mercury from a sample. As such the present invention is directed to food-grade bacteria fragments capable of binding toxic compounds found in a substance of interest.

Applications

Food-grade bacteria of the present invention may be used as a preventive measure, to prevent a subject not presently carrying a toxic compound, from acquiring the toxic compound by exposure to consumables or environments where the toxic compounds are present. Food grade bacteria of the present invention may also be used to substantially reduce or substantially eliminate toxic compounds from a subject.

Treatment of a subject carrying the toxic compounds may be accomplished to reduce or eliminate the amount of the toxic compound carried by the subject, by administering the food-grade bacteria, or extracts thereof, to the subject carrying the toxic compound.

The methods for administering food-grade bacteria may essentially be the same, whether for prevention or treatment. By routinely administering an effective dose to a subject, the risk of contamination by the undesired toxin may be substantially reduced or substantially eliminated by a combination of prevention and treatment.

In one embodiment, food-grade bacteria of the present invention may be used in methods to filter toxic compounds out of a substance. The method, in one embodiment, may comprise contacting the substance with the food-grade bacteria for a sufficient amount of time, and removing the food-grade bacteria and the toxin from the substance. To accomplish this filtration of toxic compounds from a substance, the food-grade bacteria, extracts or fragments of said food-grade bacteria capable of binding to the toxic compounds, may, for example, be attached to a filter, or to a solid support, such as an affinity column, and the substance may then be run through the filter or affinity column.

Food-grade bacteria may also be used, according to another embodiment of the present invention, to feed aquatic animals such as fish and shrimp. In one embodiment, food-grade bacteria of the present invention may, for example, be added to tanks and ponds containing the aquatic animal. Preferably the food-grade bacteria used for aquatic animals, may be a bacteria that occurs naturally in fresh and sea water environments.

Preparation and Administration

Although this invention is not intended to be limited to any particular mode of application, oral administration of the compositions are preferred. One food-grade bacterium may be administered alone or in conjunction with a second, different food-grade bacterium. Any number of different food-grade bacteria may be used in conjunction. By "in conjunction with" is meant together, substantially simultaneously or sequentially. The compositions may be administered in the form of tablet, pill or capsule, for example. One preferred form of application involves the preparation of a freeze-dried capsule comprising the composition of the present invention. Another preferred form of application involves the preparation of a lyophilized capsule of the present invention. Still another preferred form of application involves the preparation of a heat dried capsule of the present invention.

By "amount effective" as used herein is meant an amount of food-grade bacterium or bacteria, e.g., *Lactobacillus*, high enough to significantly positively modify the condition to be treated but low enough to avoid serious side effects (at a reasonable benefit/risk ratio), within the scope of sound medical judgment. An effective amount of *Lactobacillus* will vary with the particular goal to be achieved, the age and physical condition of the subject being treated, the duration of treatment, the nature of concurrent therapy and the specific *Lactobacillus* employed. The effective amount of *Lactobacillus* will thus be the minimum amount which will provide the desired detoxification.

A decided practical advantage is that the food-grade bacteria, e.g. *Lactobacillus*, may be administered in a convenient manner such as by the oral, intravenous (where non-viable), or suppository (vaginal or rectal) routes.

Depending on the route of administration, the active ingredients which comprise food-grade bacteria may be required to be coated in a material to protect said organisms from the action of enzymes, acids and other natural conditions which may inactivate said organisms. In order to administer food-grade bacteria by other than parenteral administration, they should be coated by, or administered with, a material to prevent inactivation. For example, food-grade bacteria may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport Lactobacilli or their by-products to an internal target of a host subject.

The food-grade organisms may also be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the food-grade bacteria in the required amount in the appropriate solvent with various of the other ingredients enumerated above, as required, followed by filtered sterilization. Generally, dispersions are prepared by incorporating the various sterilized food-grade bacteria into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

When the food-grade bacteria are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the food-grade bacteria may be incorporated with excipients and used in the form of ingestible tablets, buccal tablets, troches, capsules, elixirs, suspensions, syrups, wafers, and the like.

The tablets, troches, pills, capsules, and the like, as described above, may also contain the following: a binder such as gum tragacanth, acacia, corn starch or gelatin;

excipients such as dicalcium phosphate; a disintegrating agent such as corn starch, potato starch, alginic acid, and the like; a lubricant such as magnesium stearate; and a sweetening agent such as sucrose, lactose or saccharin may be added or a flavoring agent such as peppermint, oil or wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules or Lactobacilli in suspension may be coated with shellac, sugar or both.

A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the food-grade organism may be incorporated into sustained-release preparations and formulations.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the food-grade bacteria calculated to produce the desired preventive or therapeutic effect in association with the required pharmaceutical carrier. The specification for the novel dosage unit forms of the invention may be dictated by and may be directly depending on (a) the unique characteristics of the food-grade bacteria and the particular preventive, detoxification or therapeutic effect to be achieved, and (b) the limitations inherent in the art of compounding such food-grade bacteria for the establishment and maintenance of a healthy flora in the intestinal tract.

The food-grade organism is compounded for convenient and effective administration in effective amounts with a suitable pharmaceutically or food acceptable carrier in dosage unit form as hereinbefore disclosed. A unit dosage form can, for example, contain the principal active compound in an amount approximating $10^9$ viable or non-viable, e.g., Lactobacilli, per ml. In the case of compositions containing supplementary ingredients such as prebiotics, the dosages are determined by reference to the usual dose and manner of administration of the said ingredients.

The pharmaceutically acceptable carrier may be in the form of milk or portions thereof including yogurt. Skim milk, skim milk powder, non-milk or non-lactose containing products may also be employed. The skim milk powder is conventionally suspended in phosphate buffered saline (PBS), autoclaved or filtered to eradicate proteinaceous and living contaminants, then freeze dried heat dried, vacuum dried, or lyophilized.

Some other examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry, extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tabletting agents, stabilizers, anti-oxidants and preservatives, can also be present.

Accordingly, the subject may be orally administered a therapeutically effective amount of at least one food-grade bacteria and a pharmaceutically acceptable carrier in accordance with the present invention. The food-grade bacteria may be a *Lactobacillus*. The *Lactobacillus* is may be selected from the group comprising the bacteria listed in Table 1.

TABLE 1

Strains Tested For Ability to Degrade or Sequester Toxic Compounds

| Species | Strain Code 1 | Strain Code 2 |
|---|---|---|
| Lactobacillus casei | Shirota YIT 9029 | FERM BP-1366 |
| Lactobacillus casei | ATCC 393 | |
| Lactobacillus crispatus | ATCC 33323 | |
| Lactobacillus fermentum | ATCC 11739 | |
| Lactobacillus johnsonii | DSM 20553 | |
| Lactobacillus plantarum | ATCC 14917 | |
| Lactobacillus rhamnosus | ATCC 27773 | |
| Lactobacillus reuteri | RC-14 | ATCC 55845 |
| Lactobacillus amylovorus | LAB | |
| Lactobacillus rhamnosus | GG | ATCC 53013 |
| Lactobacillus rhamnosus | GR-1 | ATCC 55826 |
| Lactobacillus rhamnosus | HN001 | |
| Lactobacillus rhamnosus | R37 | DN 116-0060 |
| Lactobacillus rhamnosus | R38 | DN 116-0063 |
| Lactobacillus rhamnosus | R22 | DN 116-0009 |
| Lactobacillus rhamnosus | R17 | DN 116-0136 |
| Lactobacillus rhamnosus | R29 | DN 116-0064 |
| Lactobacillus rhamnosus | R3 | DN 116-0061 |
| Lactobacillus rhamnosus | R10 | DN 116-0032 |
| Lactobacillus rhamnosus | R11 | DN 116-0141 |
| Lactobacillus casei | C3 | DN 114-0017 |
| Lactobacillus casei | C8 | DN 114-0022 |
| Lactobacillus casei | C11 | DN 114-0125 |
| Lactobacillus casei | C26 | DN 114-0074 |
| Lactobacillus casei | C6 | DN 114-0226 |
| Lactobacillus casei | C20 | DN 114-0037 |
| Lactobacillus casei | C29 | DN 114-0230 |
| Lactobacillus casei | C13 | DN 114-0126 |
| Lactobacillus casei | C28 | DN 114-0189 |
| Lactobacillus casei | C31 | DN 114-0227 |
| Lactobacillus casei | C10 | DN 114-0223 |
| Lactobacillus casei | C1 | DN 114-0001 |

The above disclosure generally describes the present invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Demonstration of Removal of Inorganic Lead and Cadmium from an Aqueous Environment 1 mL inoculums of 24 hour cultures of *Lactobacillus rhamnosus* GR-1, *Lactobacillus casei* 393T, *Lactobacillus johnosonii* 20553 and *Lactobacillus plantarum* 14917T at cell concentrations of approx. $1 \times 10^9$ CFU/mL were added to a 50 mM HEPES buffer containing Pb or Cd and incubated for 5 hours at 37° C. Following incubation, cells were removed by centrifugation at 5,000 G. The total metal concentration in the supernatant was analyzed via Inductively Coupled Plasma—Mass Spectrometry (ICP-MS).

FIG. 1 illustrates the ability of food grade Lactobacilli to remove Pb (A) and Cd (B) from a solution at starting inoculums of 2 ppm and 2.5 ppm for lead and cadmium respectively. Depending on the species/strain of Lactobacilli examined and the metal environment there was variation in removal. As illustrated in FIG. 1 A 45-50% of Pb was removed from solution while as illustrated in FIG. 1 B 40-80% of Cd was removed. Removals of both Pb and Cd were deemed significant (p<0.05) by an ANOVA one-way analysis of variance.

Example 2

Figure 2:
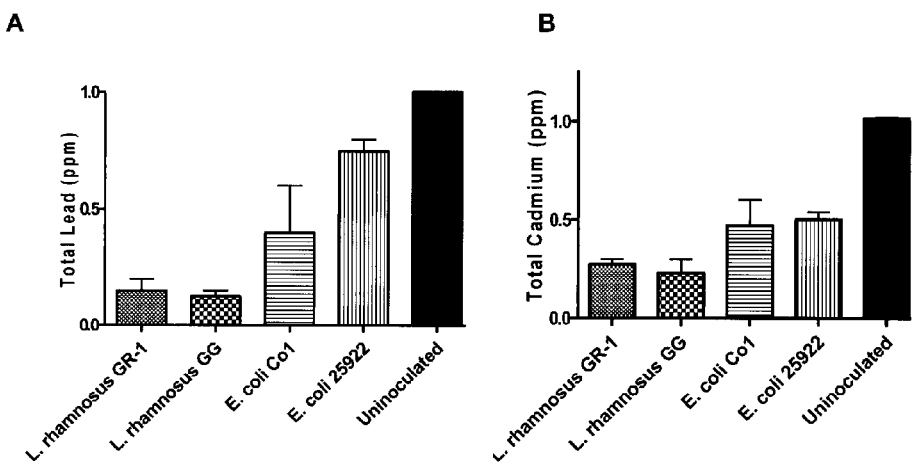
FIG. 2 A is a graph illustrating the ability of food grade Lactobacilli to remove lead (Pb) from a solution compared to E. coli (error bars±SEM).

Demonstration of Specificity of Lead and Cadmium Removal by Food Grade Lactobacilli from an Aqueous Solution 1 mL inoculums of 24 hour cultures of *Lactobacillus rhamnosus* GR-1, *Lactobacillus rhamnosus* GG, *E. coli* Col and *E. coli* 25922 at cell concentrations of approx. $1 \times 10^9$ CFU/mL were added to a 50 mM HEPES buffer containing Pb or Cd and incubated for 5 hours at 37° C. Following incubation, cells were removed by centrifugation at 5,000 G. The total metal concentration in the supernatant was analyzed via Inductively Coupled Plasma—Mass Spectrometry (ICP-MS). As illustrated in FIG. 2, for both Pb (FIG. 2 A) and Cd (FIG. 2B), Lactobacilli removed 70-80% of metal in solution while *E. coli* removal was only 30-50%. The amount removed by Lactobacilli compared to *E. coli* strains and uninoculated control were shown to be significant (P<0.05) by an ANOVA one-way analysis of variance.

Example 3

Removal of Lead and Cadmium by Live and Dead Lactobacilli

In this example, the ability of live and dead Lactobacilli to remove lead (FIG. 3 A) cadmium and (FIG. 3B) from solution at a starting inoculums of 3 ppm was tested.

Figure 3:
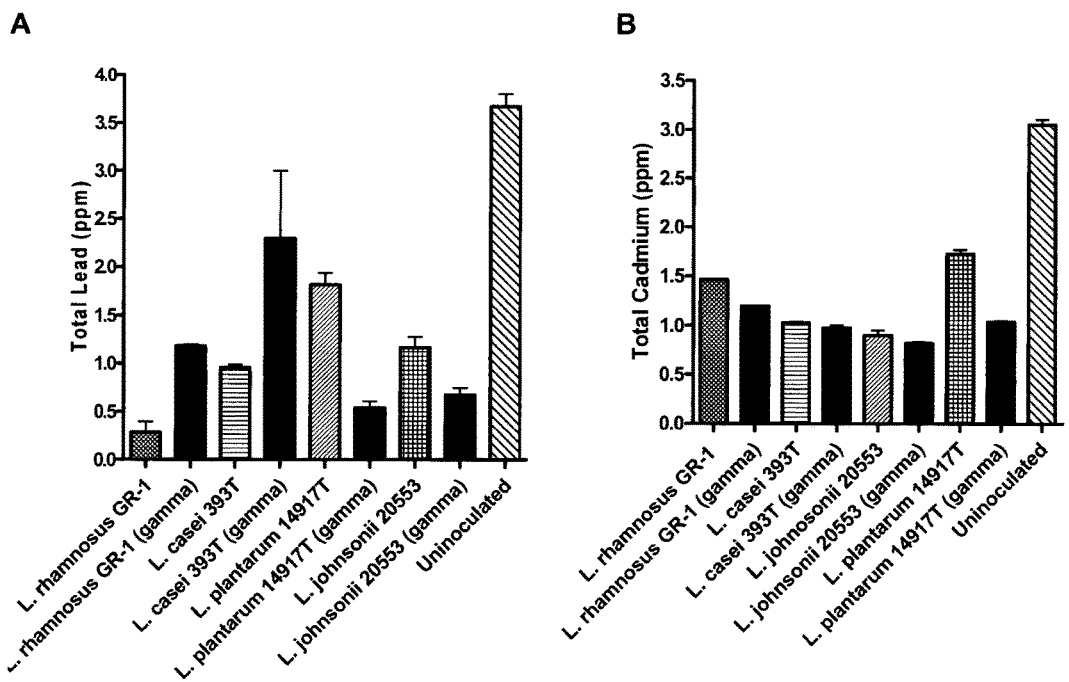
FIG. 3 A is a graph illustrating the ability of live and dead food grade Lactobacilli to remove lead (Pb) from a solution (error bars±SEM).

The assay was carried out as previously described in Examples 1 and 2. Viable cells of all Lactobacilli were compared to cells that were killed by gamma irradiation at 5.5 Kilo Grays (KG) for 1 hr. Gamma irradiation was used as it kills the cells without destroying cell wall/membrane integrity. Equal inoculums of viable and dead cells were used. With reference to FIG. 3 B, live and cells irradiated with gamma rays were able to remove roughly equal amounts of cadmium. However, as illustrated in FIG. 3 A, there was a split between the ability of viable or dead cells to bind more lead. The results obtained herein show that binding of metals may likely be a surface associated action not requiring actively metabolic cells. As such, the present invention is also directed to the parts of food-grade bacteria capable of binding heavy metals.

Example 4

Demonstration of Passive Sequestration Activity

Figure 4:
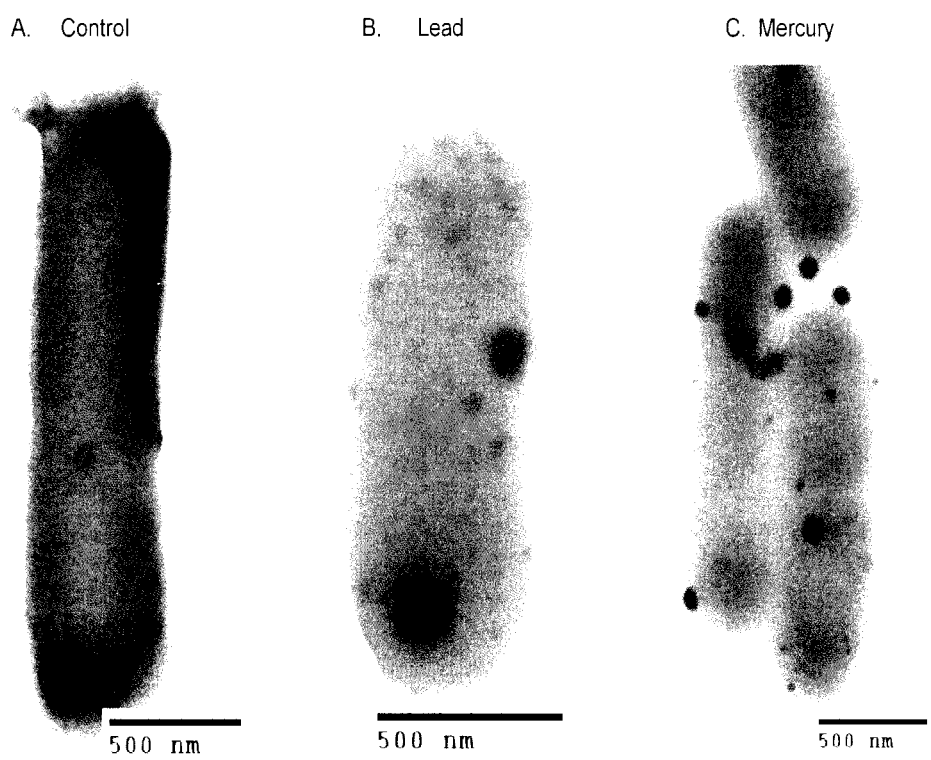
FIG. 4 are TEM microphotographs of *Lactobacillus rhamnosus* R37 incubated with a control buffer without the addition of metals (panel A), lead (panel B), and mercury (panel C).

FIG. 4 illustrates TEM micrographs of *Lactobacillus rhamnosus* R37 incubated in 50 mM HEPES-NaOH buffer (A) with 1 mM Pb (B) and 1 mM $HgCl_2$ (C) added. Numerous deposits are observed throughout the cells incubated with heavy metals (B and C) however; some smaller deposits are also visible when no metal is added (A). The nature of the deposits was confirmed using SEM and EDX analysis.

Figure 5:
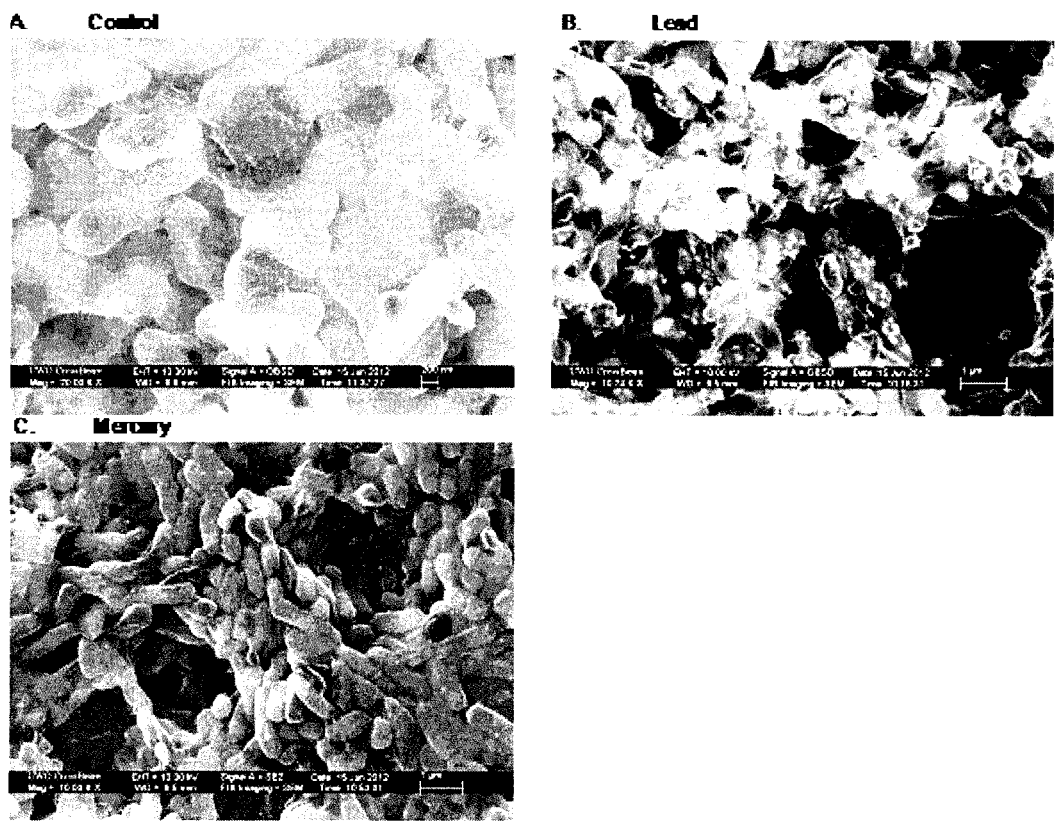
FIG. 5 are scanning electron micrographs of *Lactobacillus rhamnosus* R37 incubated with a control buffer without the addition of metals (panel A), lead (panel B), and mercury (panel C).

FIG. 5 are SEM micrographs of *Lactobacillus rhamnousus* R37 incubated in 50 mM HEPES-NaOH buffer (A) with 1 mM Pb (B) and 1 mM $HgCl_2$ (C) added. Numerous deposits are observed throughout the cells incubated with heavy metals (B and C) however, some smaller deposits are also visible when no metal is added (A).

Figure 6:
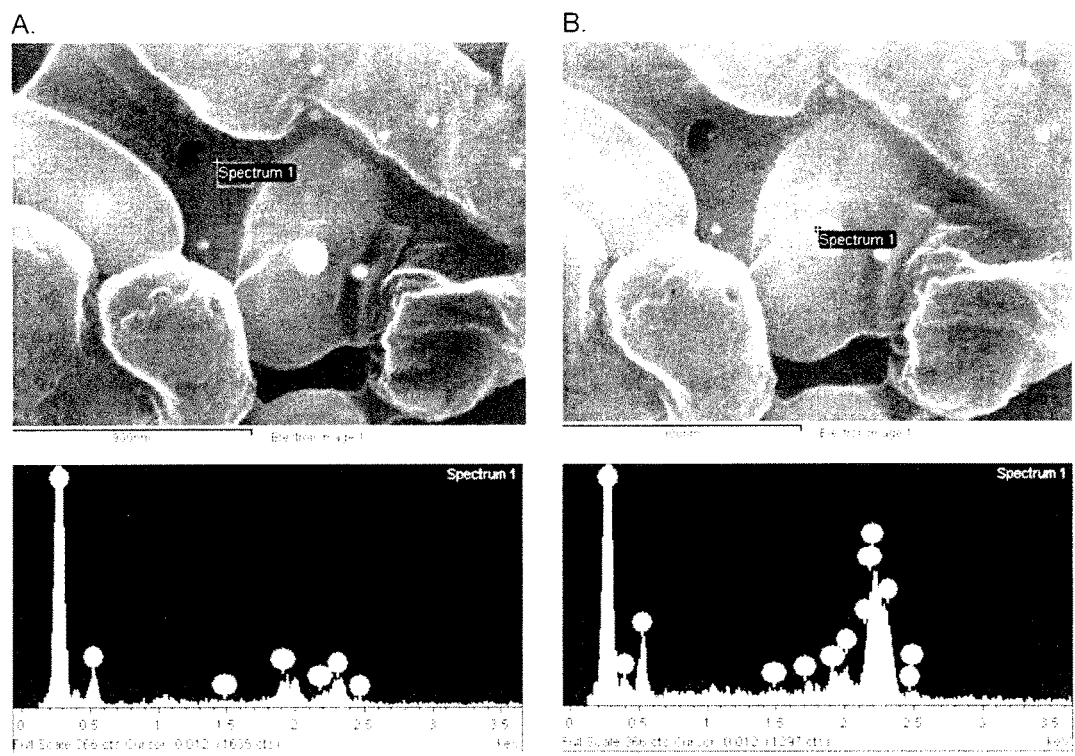
FIG. 6 A is a scanning electron micrograph of *Lactobacillus rhamnosus* R37 (top) and a corresponding energy-dispersive X-ray spectrum of a portion of a cell not containing visible deposits.

FIG. 6 illustrates energy-dispersive X-ray spectroscopy (EDX) analysis of putative metal deposits in *Lactobacillus rhamnosus* R37. Osmium coated samples being imaged with SEM were analyzed with EDX to determine the elemental composition of putative metal deposits within the cell. FIG. 6 A demonstrates the spectrum (bottom) of a portion of cell not containing any visible deposits and mercury was not detected. FIG. 6 B shows analysis of a large deposit which was determined to contain 36.62% mercury by mass proving cellular sequestration of mercury (see Table 2).

Similar results were also obtained for GR-1, R3, R39, *Lactobacillus casei* C3 showing mercury in the cell.

TABLE 2

| | Control | | Suspected Hg deposit | | |
|---|---|---|---|---|---|
| Element | Weight % | Atomic % | Element | Weight % | Atomic % |
| Carbon | 74.44 | 87.03 | Carbon | 39.67 | 70.99 |
| Oxygen | 11.75 | 10.32 | Nitrogen | 7.51 | 11.52 |
| Sulfur | 4.50 | 1.97 | Oxygen | 8.51 | 11.44 |
| Osmium | 9.30 | 0.69 | Phosphorus | 1.23 | 0.85 |
| Totals | 100.00 | 100.00 | Sulfur | 0.97 | 0.65 |
| | | | Osmium | 5.50 | 0.62 |
| | | | Mercury | 36.62 | 3.92 |
| | | | Totals | 100.00 | 100.00 |

Example 5

Confirmation of Precipitation and Binding of Metals on and within Food Grade Bacteria Lactobacilli were incubated in a 50 mM HEPES buffer for 2 hrs at 37° C. in the presence of metals at a final concentration of 10 mM. The assay was carried out by incubating bacteria (*Lactobacillus rhamnousus* GR-1) for 2 hrs in a 10 mM metal solution at 37° C. Following incubation the bacteria were diluted 100-fold and filtered through a 0.2 μm filter to trap bacteria and allow passage of solution. The filters were dried at room temperature for 2 hrs and then coated with 5 nm of osmium tetra oxide. The identification of the metals was confirmed by EDAX X-ray analysis which showed that the metal precipitates were the heavy metals added to solution.

Figure 7:
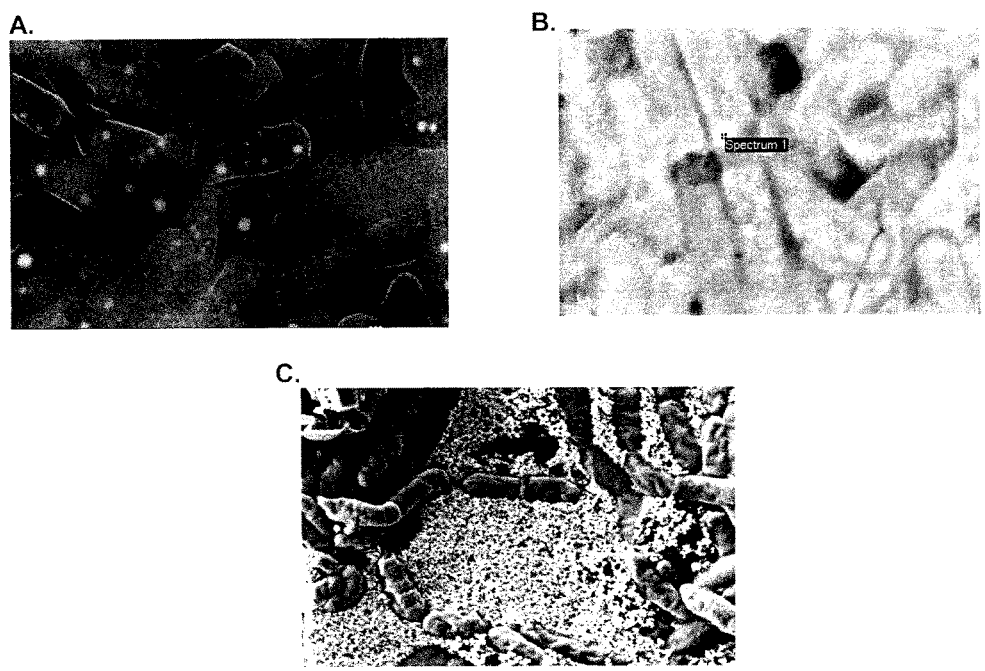
FIG. 7 are scanning electron microphotographs of *Lactobacillus rhamnosus* GR-1 incubated with lead (panel A), cadmium (panel B), and a control without the addition of metals (panel C).

FIG. 7 are scanning electron micrographs (SEM) of *Lactobacillus rhamnosus* GR-1 incubated with (A) lead or (B) cadmium. The bright spots observable in the images represent the precipitation of heavy metal particles on the surface and inside the cell. FIG. 7 (C) displays the non metal control which is the Lactobacilli without addition of metals, note the absence of precipitate metal particles.

Example 6

Preliminary Evidence of Protective Effect of Food Grade Lactobacilli on a Caco-2 Cell Line as a Model of the Gut Epithelial Barrier Caco-2 cells were grown in 12 or 24 well plates for two weeks using supplemented Eagles Minimum Essential Medium (ATCC®) as described above. At two weeks, media was aspirated and cells were washed lightly 2× with warm 50 mM HEPES buffer. Bacterial cultures of interest were also grown in 5 mL broth cultures for 22 hrs and washed 2× with 50 mM HEPES. Bacterial cells were resuspended to 10 mL in Eagles Minimum Essential Medium (ATCC®) without any Pen/Strep in solution, 400 µL of media was added to wells in 24 well plates and 900 µL of media was used in 12 well plates. Bacteria were allowed to incubate with cell line for 2 hr at 37° C. During incubation period metal spiked solutions of Eagles Minimum Essential Medium (ATCC®) was made by adding stock concentrations of Pb, Cd or As (Sigma Aldrich®) to the media at desired concentrations. Following incubation period the bacterial metal solution was aspirated so that only cells adhering to the Caco-2 cell monolayer remained, the media was replaced with the metal spiked media in addition control wells were set up that either did not have metal in the media and were not incubated with bacterial species. Cells were incubated for 5 hrs in metal spiked media at 37° C.

Figure 8:
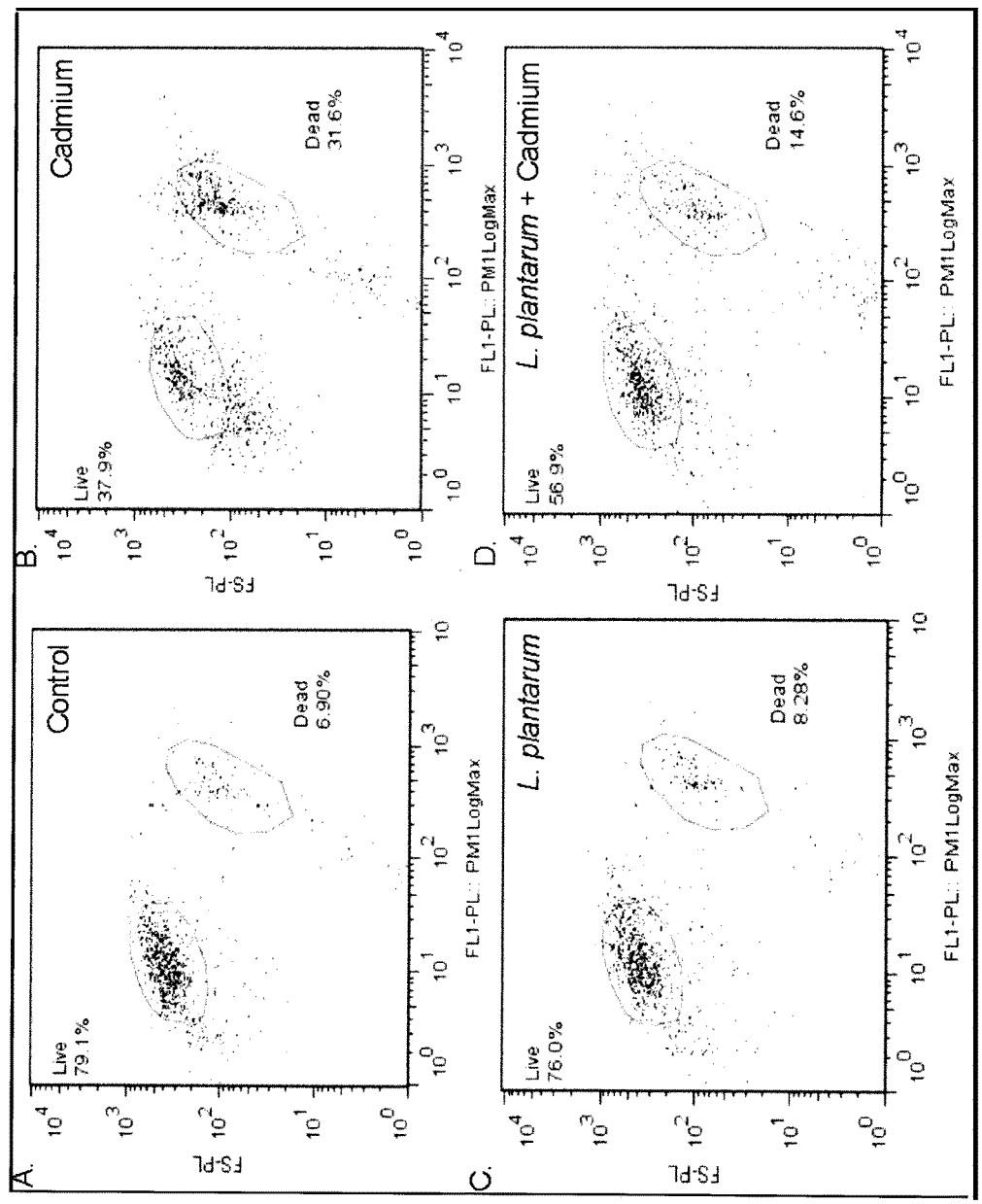
FIG. 8 is a flow cytometry analysis of Caco-2 cell line comparing viability vs. mortality of untreated cells (panel A), cells exposed to cadmium (panel B), cells exposed to *Lactobacillus plantarum* 149171 (panel C), and cells exposed to *Lactobacillus plantarum* 14917T and then exposed to cadmium (panel D).

Following this incubation, media was removed by aspiration and discarded. Cells were washed once gently with warm HEPES buffer and then removed from the wells using 500 ul of 0.25% (w/v) trypsin until cells detached from flask. 500 µL of cell media was added to stop trypsin reaction and total volume of each well was transferred into separate sterile 1.5 mL centrifuge tubes (Diamed®). The cell suspension was mixed by pipetting to avoid formation of bubbles. Cells were centrifuged in a bench top microcentrifuge for 2 mins at 120 RPM, supernatant was discarded and cells were suspended in 1×PBS. Cells were diluted by a factor of 10 by suspending 50 µL of cells with 450 µL of Guava Viscount® Reagent (Cat No. 4000-0041) in a clean sample tube, cells were stained for at least 5 min. Stained cells were then analyzed for viability using the Guava ViaCount Assay on the Guava EasyCyte Mini bench top flowcytometer. Cells were separated based on viability forming two distinct populations: live and dead. Populations were analyzed and statistically compared using FlowJo (TreeStar®) analysis software for flow cytometry data. Cells were analyzed to see differences in viability after exposure to metals in the presence or absence of Lactobacilli FIG. 8 illustrates a flow cytometry analysis of the Caco-2 cell line comparing viability vs. mortality for (A) un treated cells, (B) Caco-2 cells exposed to cadmium, (C) taco-2 cells exposed to *Lactobacillus plantarum* 14917T and (D) Caco-2 cells pretreated with *Lactobacillus plantarum* 14917T and then exposed to cadmium. As shown by (D) addition of *Lactobacillus plantarum* 14917T before cadmium exposure contributed to increased survival of the cell line then when just exposed to cadmium (B).

Example 7

Viability of Lead and Cadmium Resistant Food Grade Bacteria of the Genus *Lactobacillus*

The assay was carried out by inoculating a 200 µL well of Man Rogosa Sharpe (MRS) medium containing lead or cadmium at a concentration of 100 ppm with an inoculum of $10^7$ bacteria from a fresh 24 hrs broth cultures of the Lactobacilli species *Lactobacillus rhamnosus* and *Lactobacillus plantarum* 14917T. Growth was measured by OD600 for 24 hrs. incubation at 37° C. Growth was measured for 24 hours with readings taken every 30 minutes by optical density measurements at a wavelength of 600 nm. Following the growth assay all species were diluted and drop plated on MRS agar to determine colony forming units (CFU) in solution.

Figure 9:
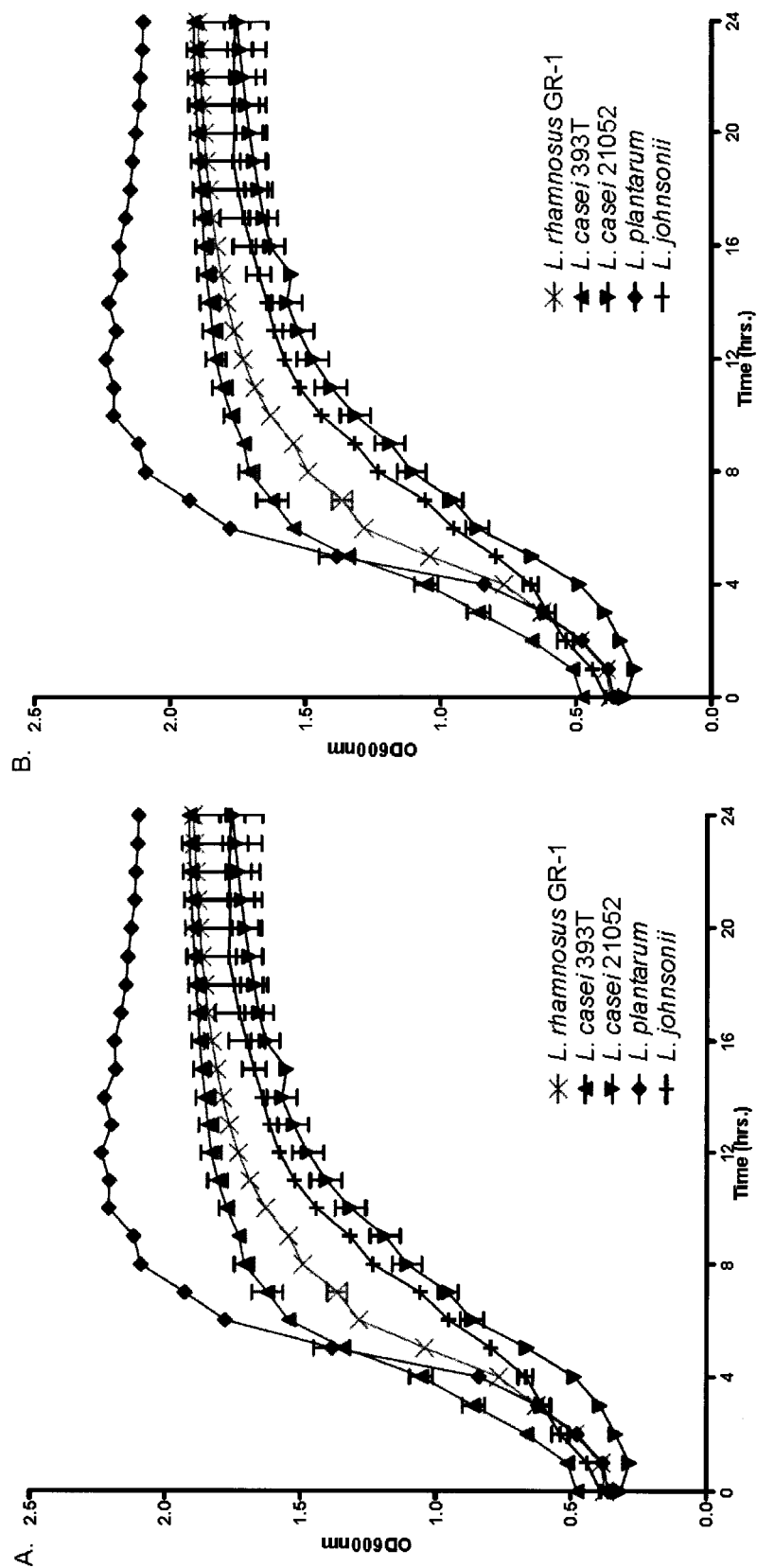
FIG. 9 A is a graph illustrating the growth of a number of Lactobacilli species in Man Rogosa Sharpe (MRS) media having lead.

FIG. 9 shows growth of all tested Lactobacilli species in the MRS media with lead (FIG. 9 A) or cadmium (FIG. 9 B) at a concentration of 100 ppm.

Example 8

Demonstration of Removal of Inorganic Mercury from an Aqueous Environment

Figure 10:
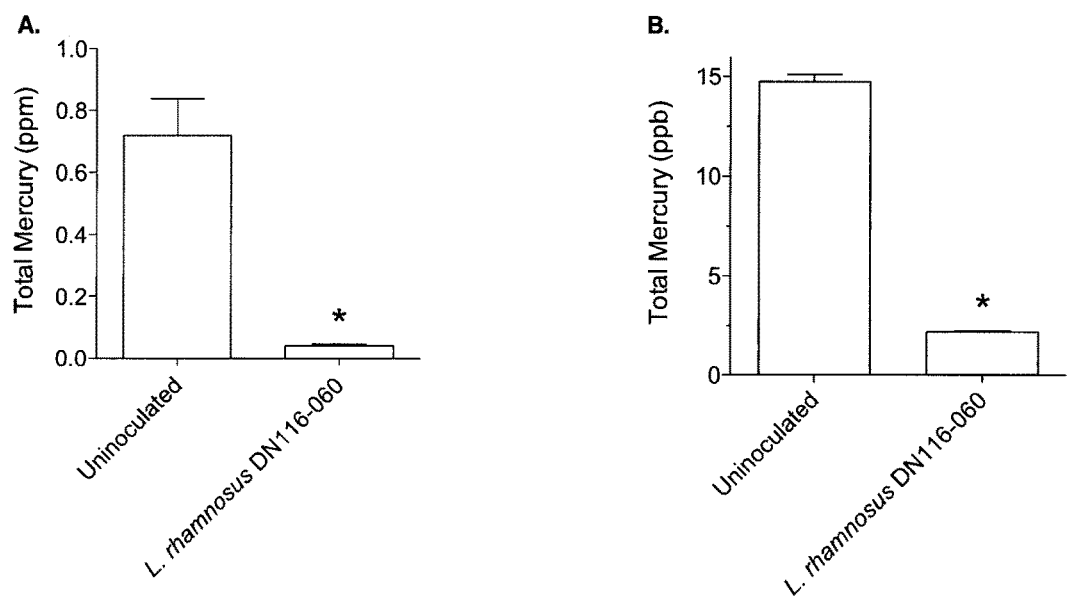
FIG. 10 A is a graph illustrating the ability of a food grade bacterium of the present invention to remove $Hg^{2+}$ from a solution having a 1 part per million (ppm) $Hg^{2+}$ inoculum (error bars±SEM; * signifies significant (p<0.05) difference by an unpaired T-test).

A 1% inoculum of a 24 hour culture of *Lactobacillus rhamnosus* DN116-060 was added to de Man Rogosa Sharpe (MRS) broth containing $HgCl_2$ and incubated for 24 hours at 37° C. Following incubation, cells were removed by centrifugation at 5,000 g. The total mercury concentration in the supernatant was analyzed via cold vapor atomic absorption spectroscopy (CVAAS). As illustrated in FIG. 10, the Lactobacilli removed 94.4% of a 1 part per million (ppm) mercury inoculum (FIG. 10 A) and 85% of a 15 part per billion (ppb) inoculum (FIG. 10 B). Both removals were deemed significant (p<0.05) by an unpaired T-test.

Example 9

Demonstration of Removal of Organic Mercury Form an Aqueous Environment

A 1% inoculum of a 24 hour culture of *Lactobacillus rhamnosus* DN116-060 was added to de Man Rogosa Sharpe (MRS) broth containing MeHgCl2 and incubated for 24 hours at 37° C. Following incubation, cells were removed by centrifugation at 5,000 g. The total mercury concentration in the supernatant was analyzed via cold vapor atomic absorption spectroscopy (CVAAS).

Figure 11:
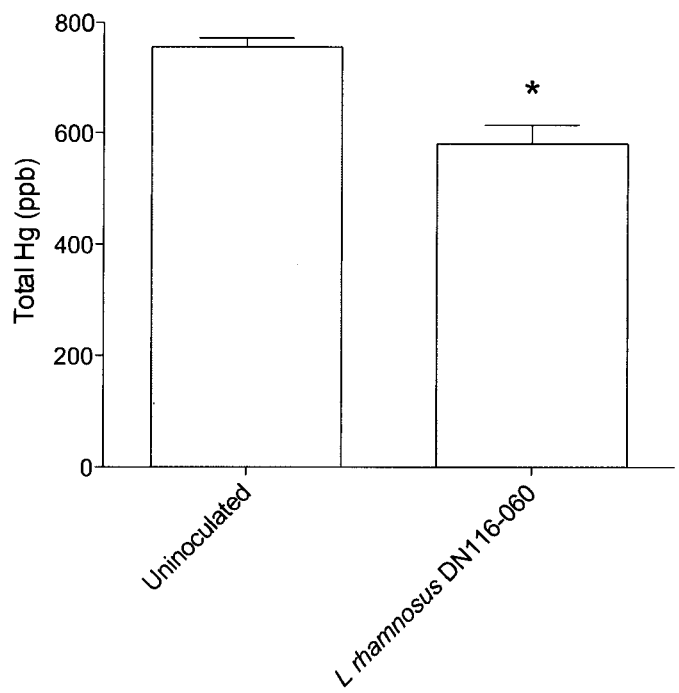
FIG. 11 is a graph illustrating the ability of a food grade bacterium of the present invention to remove organic mercury from a solution (error bars±SEM; * signifies significant (p<0.05) difference by an unpaired T-test).

FIG. 11 shows the ability of a food grade bacterium to remove $MeHg^{2+}$ from solution at a starting inoculum of 1 ppm MeHgCl2. (Error bars±SEM). As illustrated in FIG. 11, the Lactobacilli removed 23.2% of a 1 ppm mercury inoculum (p<0.05 by an unpaired t-test).

Example 10

Inorganic Mercury Removal by Live and Dead *Lactobacillus rhamnosus* DN116-060

The assay was carried out as previously described in Example 9 at a concentration of 500 ppb $HgCl_2$. Viable cells of *Lactobacillus rhamnosus* DN116-010 were compared to cells that were killed by heating at 80° C. for 10 minutes at an inoculum equivalent to the final cell density of viable cells.

Figure 12:
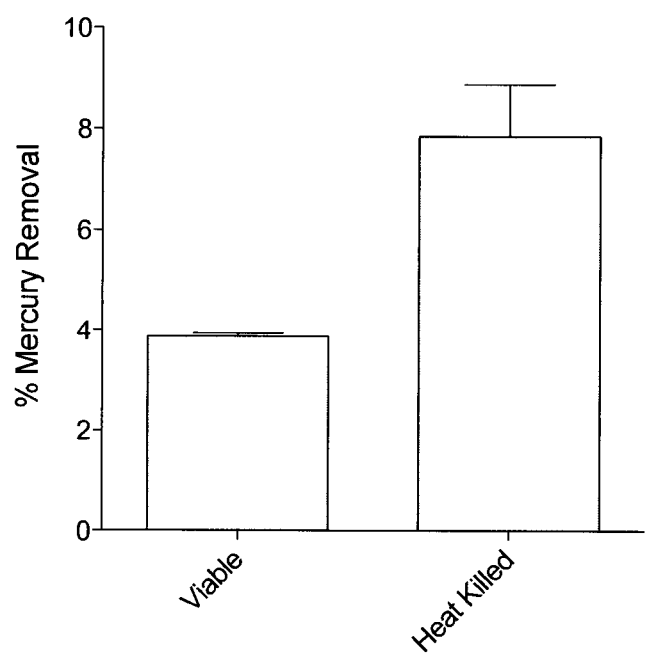
FIG. 12 is a graph illustrating the ability of live and dead food grade bacterium of the present invention to remove inorganic mercury from a solution (error bars±SEM; * signifies significant (p<0.05) difference by an unpaired T-test).

FIG. 12 illustrates the ability of live and dead *Lactobacillus rhamnosus* DN116-060 to remove $Hg^{2+}$ from solution at a starting inoculum of 500 ppb $HgCl_2$. As shown in FIG. 12, viable cells were capable of removing significantly more mercury than heat killed cells (p<0.05 by unpaired t-test)

suggesting that there is a passive sequestering of mercury as well as potential metabolic detoxification.

Example 11

Variability of Mercury Resistance within Food Grade Bacteria of the Genus *Lactobacillus*

Assay was carried out as previously described in Example 9 across a spectrum of $HgCl_2$ concentrations. Growth was measured after 24 hours at 37° C. by the optical density of cultures at a wavelength of 600 nm. A spectrum of resistances to mercury were observed in both species demonstrating that resistance to mercury is a variable trait among food grade bacteria.

Figure 13:
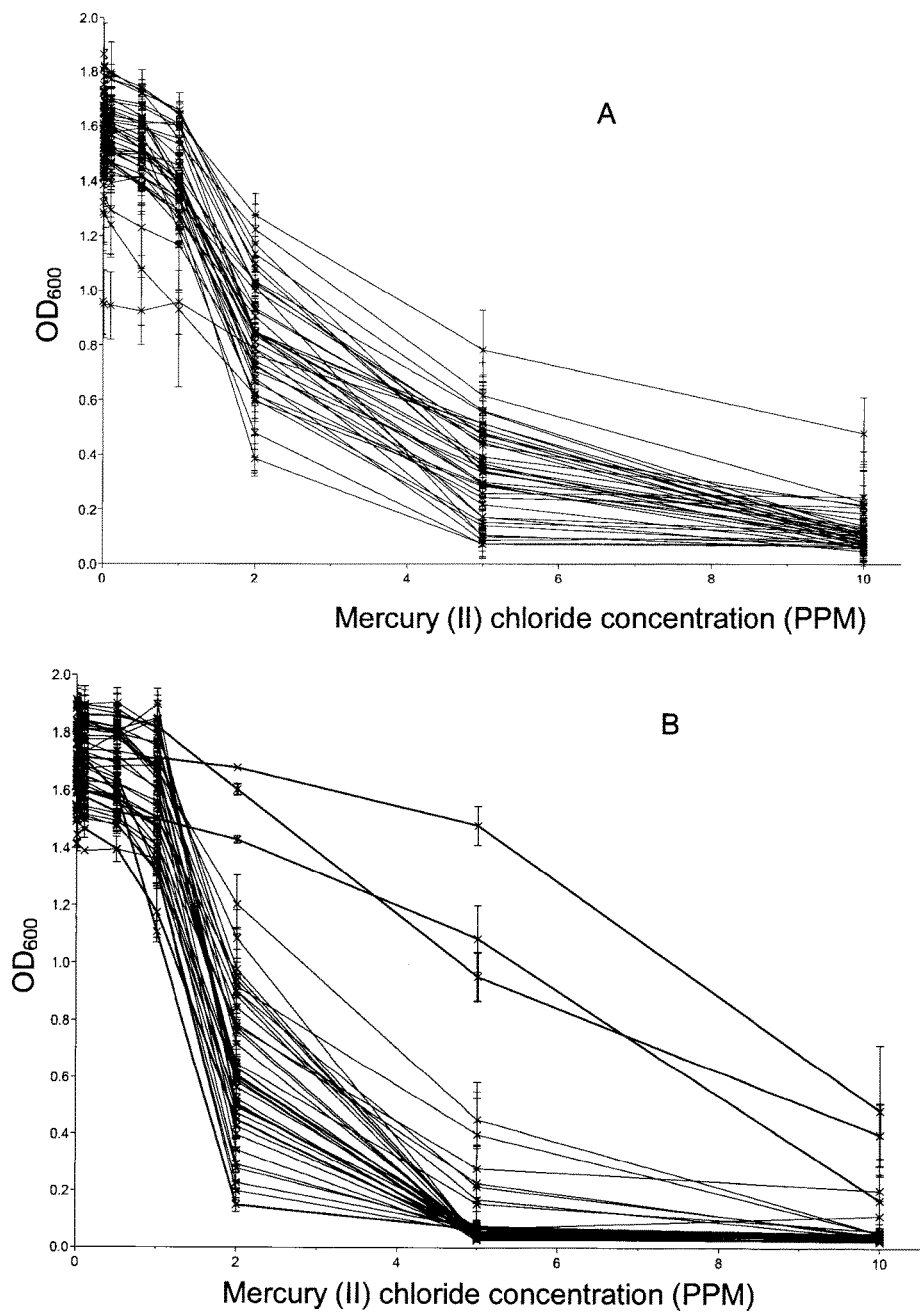
FIG. 13 is a graph illustrating variability of mercury resistance within a group of food grade bacteria of the genus *Lactobacillus*. Panel A illustrates growth of different strains of *Lactobacillus casei* in a gradient of $Hg^{2+}$ and panel B illustrates growth of different strains of *Lactobacillus rhamnosus* in a gradient of $Hg^{2+}$.

FIG. 13 illustrates the growth of *Lactobacillus casei* (n=38) (FIG. 13 A) and *Lactobacillus rhamnosus* (n=40) (FIG. 14 B) in a gradient of $Hg^{2+}$ measured by OD600 after 24 hours incubation at 37° C. Each set of connected points represents one strain. Resistance is a strain variable trait resulting in a spectrum of resistance profiles in both species. FIG. 13 B illustrates three *Lactobacillus* rhamnosus strains showing a distinctly higher resistance as compared to the rest of the strains.

Example 12

Figure 14:
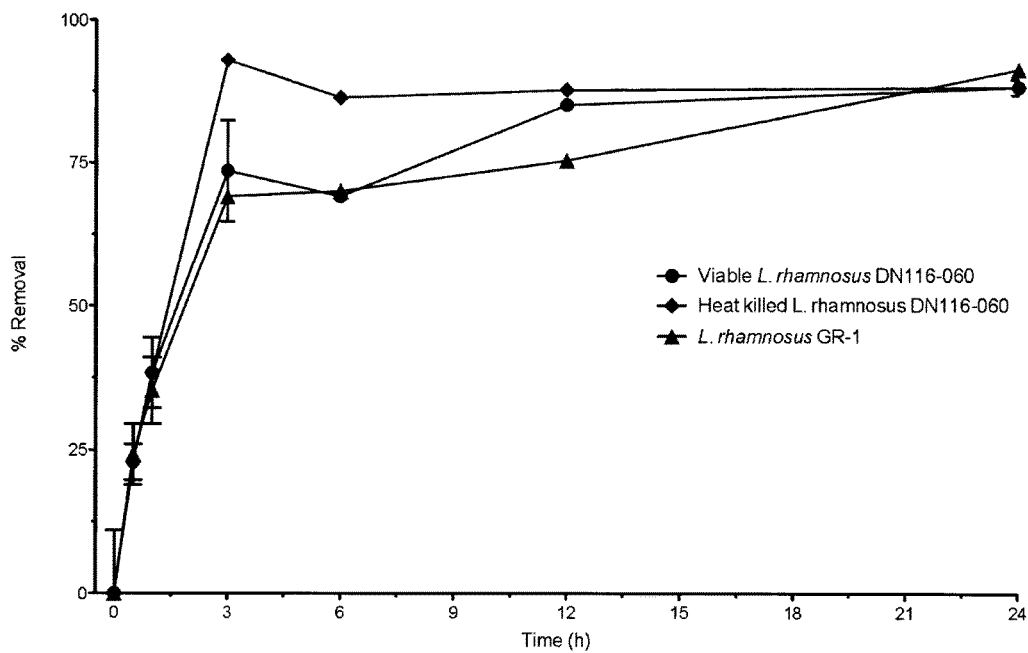
FIG. 14 is a graph illustrating twenty-four hour time course of mercury removal by *Lactobacillus rhamnosus* R37 and GR-1 in HEPES-NaOH supplemented with 1 µg/mL $HgCl_2$ incubated at 37° C.

Twenty-four hour time course of mercury removal by *Lactobacillus rhamnosus* R37 (in viable and heat killed form) and GR-1 in HEPES-NaOH supplemented with 1 µg/mL $HgCl_2$ incubated at 37° C. With reference to FIG. 14, sequestration activity is not instantaneous and reaches a maximum after 12 h in *Lactobacillus rhamnosus* R37 while maximal removal was observed at 24 hours in the case of *Lactobacillus rhamnosus* GR-1.

Example 13

Resistant Strains of Food Grade Bacteria Remove More Mercury than Mercury Sensitive Strains The assay described in Example 1 was carried out using a selection of *Lactobacillus rhamnosus* strains of increased resistance and increased sensitivity to mercury.

Figure 15:
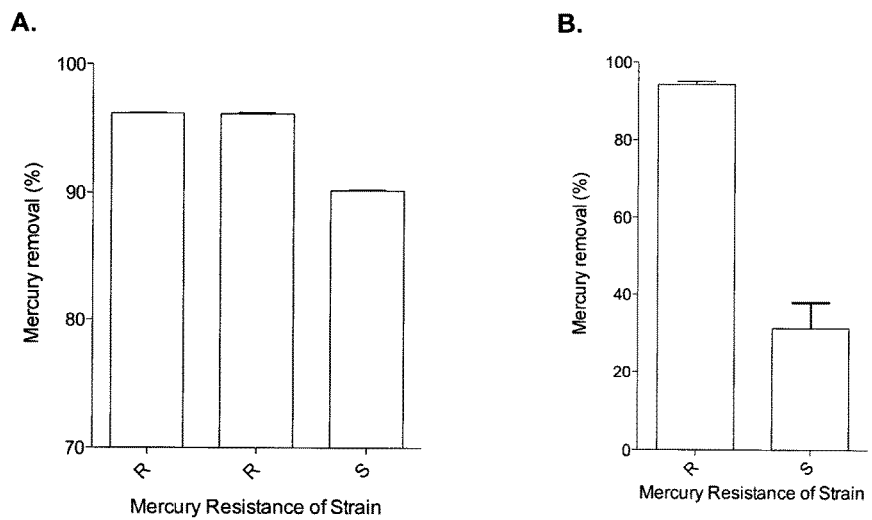
FIG. 15 are graphs illustrating removal of mercury from solution by a selection of *Lactobacillus rhamnosus* strains of increased resistance (R) and strains of increased sensitivity (S) to mercury at $HgCl_2$ concentrations of 0.5 ppm (panel A) and 1 ppb (panel B).

FIG. 15 illustrates removal of mercury from solution by a selection of *Lactobacillus rhamnosus* strains of increased resistance (R) and strains of increased sensitivity (S) to mercury at $HgCl_2$ concentrations of 0.5 ppm (FIG. 15 A) and 1 ppb (FIG. 15 B). Resistant strains removed significantly more mercury from solution than their sensitive counterparts ($p<0.05$ as determined by ANOVA with Bonferroni post test [FIG. 15A] and un-paired t-test [FIG. 15B]). (Error bars±SEM)

Example 14

Removal of Arsenite and Arsenate from an Aqueous Environment

Bacterial cultures were grown for 24 hrs in preferential media; Man Rogoas Sharpe (MRS) broth for Lactobacilli and Luria—Bertani (LB) broth for *E. coli*.

Figure 16:
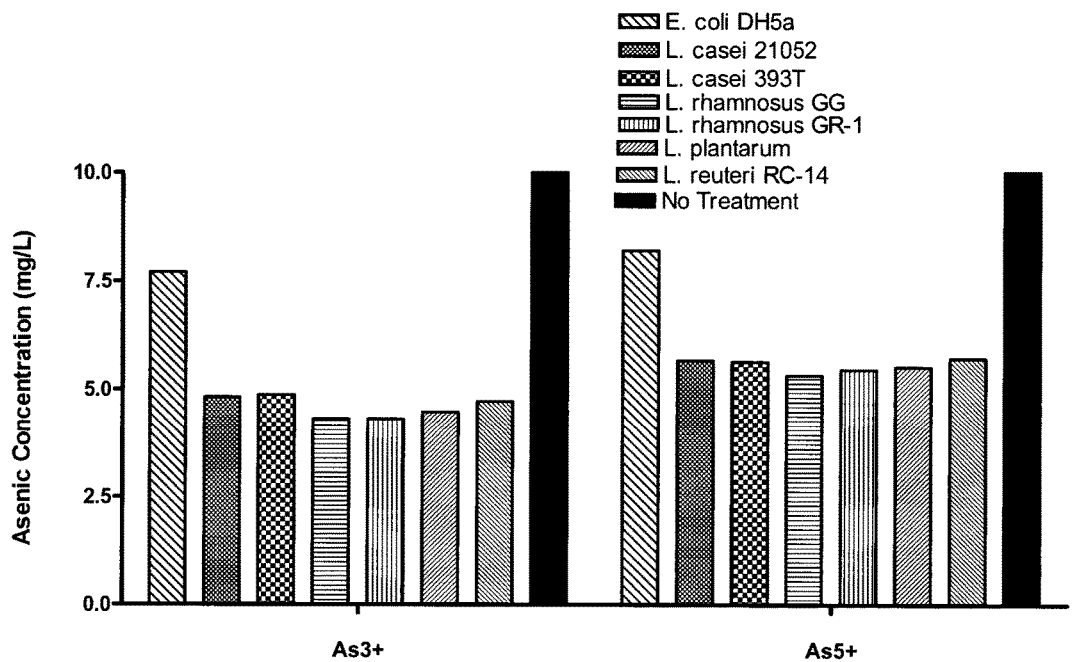
FIG. 16 is a graph illustrating the ability of food grade bacteria and E. coli species to remove As (III) and As (V) from solution at starting inoculums of 10 ppm.

Cells were centrifuged, washed and re-suspended in PBS. 1 mL aliquouts were distributed between sample tubes containing 9 mL of PBS buffer spiked with arsenic, 1 mL of MRS or LB broth was added to sample tubes. Cells were incubated for 5 hrs at 37° C.; following incubation cells were removed by centrifugation at 5,000 g. The total arsenic remaining in solution was analyzed via inductively coupled plasma—mass spectrometry (ICP-MS). As illustrated in FIG. 16 Lactobacilli were able to remove 50-60% of As (III) and As (V) while *E. coli* DH5α was less effective.

Example 15

Demonstration of Removal of Arsenite (as III) by a Panel of Lactobacilli

The assay was carried out by inoculating a 1 ppm ($9.08 \times 10^{18}$ free atoms) arsenite solution (HEPES buffer) with $1 \times 10^9$ CFU/mL of selected Lactobacilli. The solutions were incubated for 5 hrs at 37° C.; following incubation cells were removed by centrifugation at 5,000 g. The total arsenic remaining in solution was analyzed via inductively coupled plasma—mass spectrometry (ICP-MS).

Figure 17:
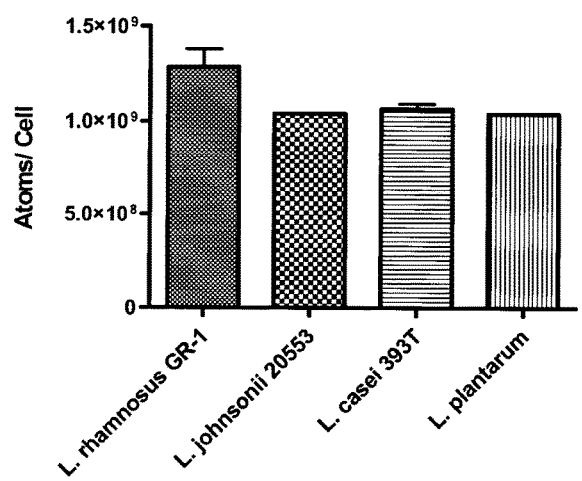
FIG. 17 is a graph illustrating the ability of food grade bacteria to remove As (III) from solution at a starting inoculums of 1 ppm. (Error bars±SEM).

As shown in FIG. 17 and Table 3, Lactobacilli removed 11-13% of the total arsenic which was determined by looking at differences in concentrations in total free atoms in solution vs. bound to each species.

TABLE 3

| Species | % Removed |
|---|---|
| *L. rhamnosus* GR-1 | 13 |
| *L. johnsonii* 20553 | 11 |
| *L. casei* 393T | 11 |
| *L. plantarum* 14917T | 11 |

Example 16

Demonstration of Removal of Arsenic (III) at High Concentrations by Lactobacilli The assay was carried out by inoculating a 100 ppm arsenite solution of HEPES buffer with $1 \times 10^9$ CFU/mL of the selected Lactobacilli. The solutions were incubated for 5 hrs at 37° C.; following incubation cells were removed by centrifugation at 5,000 g. The total arsenic remaining in solution was analyzed via inductively coupled plasma—mass spectrometery (ICP-MS).

Figure 18:
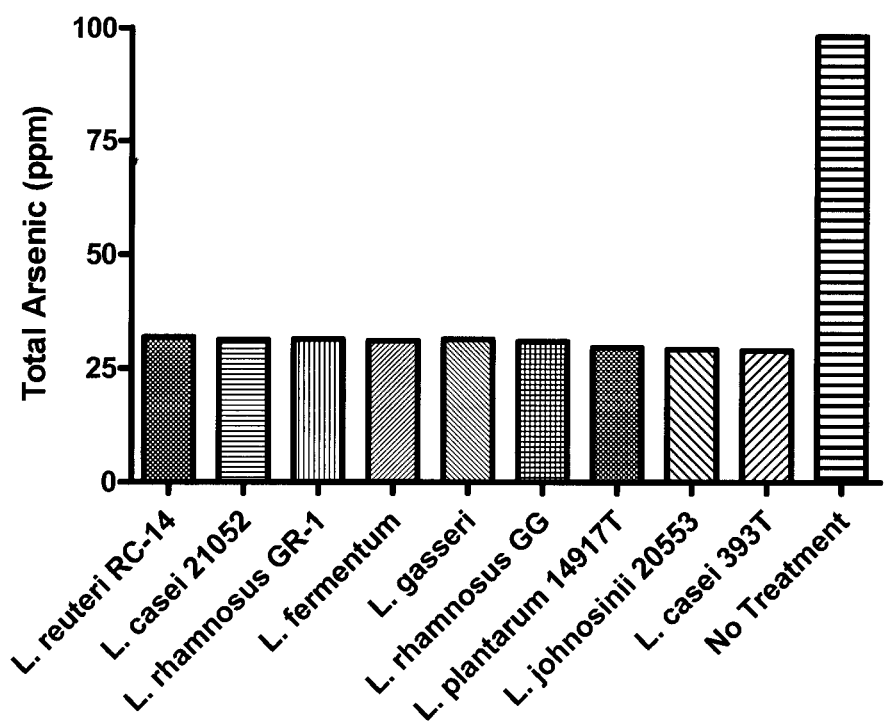
FIG. 18 is a graph illustrating the ability of Lactobacilli to remove As (III) from solution at starting inoculums of 100 ppm.

As shown in FIG. 18, all Lactobacilli showed ability to remove near 70% of arsenic from solution compared to the untreated control sample. Species to species variation in amount of arsenic able to remove was low and not significant.

Example 17

Demonstration of Removal of Malathion and Parathion from Aqueous Environment by Probiotic Bacteria Bacterial broth cultures of *Lactobacillus rhamnosus* GR-1 were grown for 24 hrs in Man Rogosa Shame (MRS) broth. Cells were collected, washed and re-suspended in a 1×PBS buffer. 1 mL of cell suspension was transferred into sample tube containing a 50:50 mixture of HEPES buffer having the pesticides and MRS. Starting inoculums of pesticides for malathion and parathion was 5 µg/L of HEPES-buffer and 0.5 µg/L of HEPES buffer respectively. Samples were incubated for 5 hrs at 37° C. Following incubation cells were removed by centrifugation at 5,000 g. The remaining pesticide in solution was analyzed via gas chromatography—mass spec (GC-MS) and values were compared to untreated controls.

Figure 19:
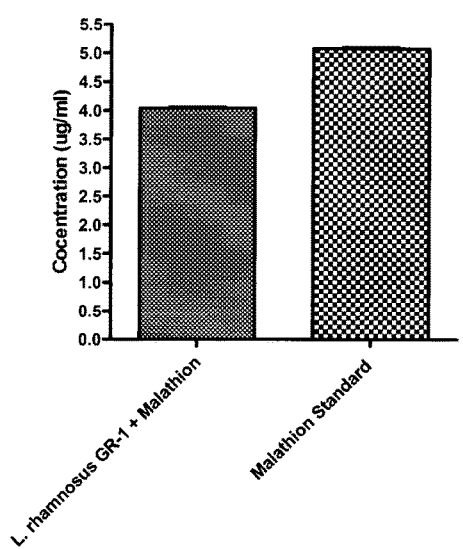
FIG. 19 is a graph depicting the ability of probiotic bacteria to remove malathion (FIG. 19 A) and parathion (FIG. 19 B) from solution. Starting inoculums for malathion and parathion are 5 µg and 0.5 µg respectively. (Error bars±SEM).
Figure 19:
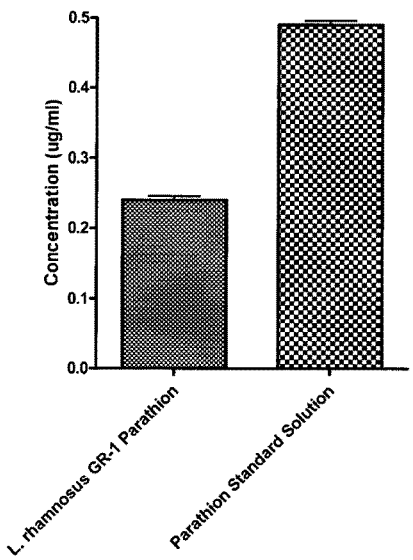

With reference to FIG. 19, *Lactobacillus rhamnosus* GR-1 was able to remove 20% of the malathion from solution (19 A) and 50% of the parathion (19 B).

Example 18

Demonstration of Removal of Malathion and Parathion Simultaneously by a Probiotic Bacterium Bacterial broth cultures of *Lactobacillus rhamnosus* GR-1 were grown for 24 hrs in Man Rogosa Sharpe (MRS) broth. Cells were collected, washed and re-suspended in a 1×PBS buffer. 1 mL of cell suspension was transferred into sample tube containing a 50:50 mixture of HEPES buffer having the pesticides and MRS. Starting inoculums of pesticides for malathion and parathion was 5 µg/L of HEPES buffer and 0.5 µg/L of HEPES buffer respectively. Samples were incubated for 5 hrs at 37° C. Following incubation cells were removed by centrifugation at 5,000 g. The remaining pesticide in solution was analyzed via gas chromatography—mass spec (GC-MS) and values were compared to untreated controls.

Figure 20:
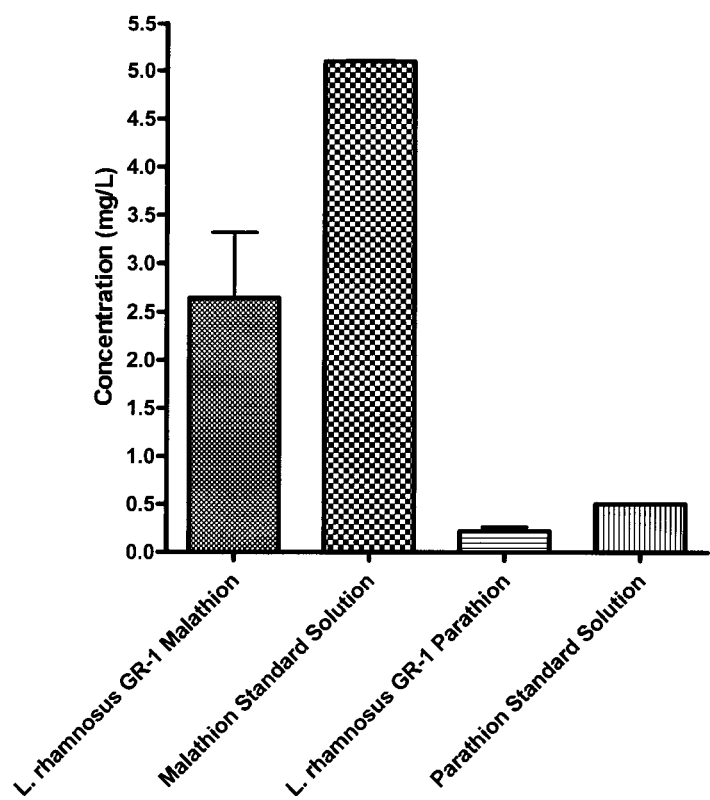
FIG. 20 is a graph illustrating the ability of a probiotic bacterium to remove both malathion and parathion from solution simultaneously. Malathion original concentration was 5 µg while parathion was 0.5 µg. (Error bars±SEM).

As shown in FIG. 20, *Lactobacillus rhamnosus* GR-1 was able to remove 50% of the malathion from solution and 50% of the parathion.

Example 19

Demonstration of Removal of Pesticides by a Panel of Food Grade Bacteria and Some *E. coli* Species Bacterial broth cultures of Lactobacilli were grown for 24 hrs in Man Rogosa Sharpe (MRS) broth, *E. coli* species were grown for 24 hours in Lucelia Broth (LB). Cells were collected, washed and re-suspended in a 1×PBS buffer. 1 mL of cell suspension was transferred into sample tubes containing a 50:50 mixture of HEPES buffer having the pesticide and MRS or LB. Starting inoculums of pesticides for malathion and parathion was 10 mg/L of HEPES buffer and 3 mg/L of HEPES buffer respectively. Samples were incubated for 5 hrs at 37° C. Following incubation cells were removed by centrifugation at 5,000 g. The remaining pesticide in solution was analyzed via gas chromatography mass spec (GC-MS) and values were compared to untreated controls.

Figure 21:
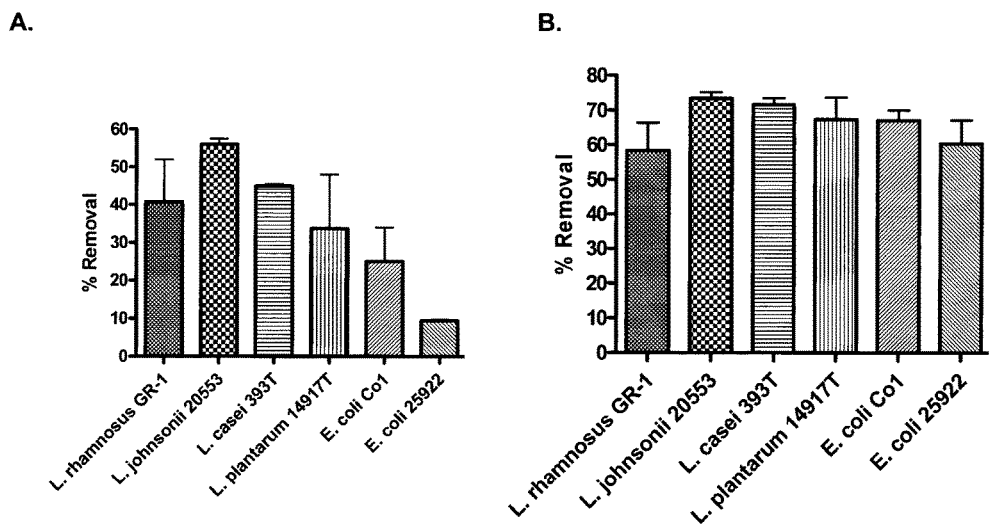
FIG. 21 is a graph depicting the ability of food grade bacteria and E. coli to remove malathion (FIG. 21 A) or parathion (FIG. 21 B) from solution. Starting inoculums of pesticides for malathion and parathion was 10 mg/L and 3 mg/L respectively. (Error bars±SEM).

FIG. 21 A illustrates that the Lactobacilli were able to remove 35-60% of malathion, while *E. coli* was able to remove 10-25% of malathion. FIG. 21 B illustrates that the Lactobacilli and *E. coli* were able to remove 55-70% of parathion.

Example 20

Demonstration of Removal of Endotoxins by a Panel of Food Grade Bacteria

Endotoxins are well known toxins responsible for sepsis and death. They are produced by a number of Gram negative bacteria and to date few effective treatments have been developed. Other potent toxins produced by bacteria include the fatal Shiga toxin produced by *E. coli* 0157:H5, and TcdA and TcdB toxins from *Clostridium difficile* both of which damage the human colonic mucosa and are potent cytotoxic enzymes. Deaths from *C. difficile* toxins have become a major concern in North American hospitals and care homes. Probiotic therapy has shown great promise in preventing infections caused by *E. coli* 0157:H7 and *C. difficile*.

Alkaline phosphatase levels (activity and protein) can be measured in feces and blood as it has been shown that up-regulation of this enzyme can detoxify endotoxins in the gut and improve gut permeability. A pig model is used for this assay, *C. difficile* toxins will be detected from stool by a commercially available enzyme-linked fluorescence immunoassay.

Example 21

Demonstration of Removal of Aflatoxin by a Panel of Food Grade Bacteria

Aflatoxin (a hepatic carcinogen) is important contributors to disease, albeit risk of exposure to the mainstay population in N. America is low. Aflatoxin B1 has been included because probiotics can have an effect against it, and such results have implications for many sub-populations in the US (eg large farming communities) and beyond (eg Middle East, Argentina).

The aflatoxin will be measured from blood by affinity column cleanup and LC-MS/MS fluorescence.

Example 22

Demonstration of Removal of Heterocyclic Aromatic Amines (HAA) by a Panel of Food Grade Bacteria Heterocyclic aromatic amines (HAA) are found in food (eg processed meat) and cause diet-related mutagenesis which plays an etiologic role in chronic diseases, including cardiovascular disease and cancer. Their direct association with cancer is low, but the potential for them to be inhibited by probiotics makes them worth studying, as a positive detox effect provides a good consumer message.

They will be measured from urine and blood samples using HPLC.

Example 23

Demonstration of Removal of Acrylamide by a Panel of Food Grade Bacteria

Acrylamide is made industrially but is highly regulated due to its neurotoxicity. It naturally forms in certain foods, particularly plant-based foods that are rich in carbohydrates and low in protein, during processing or cooking at high temperatures (French fries, potato chips). Also found heavily in cigarette smoke. Acrylamide is monitored and studied by Health Canada, but no levels have been established on what is toxic/safe, so it's tough to set a limit' or even tell in a study what would be considered dangerous. It has a link to causing cancer and information on how much will cause this effect is not known.

Acrylamide will be detected by HPLC.

We claim:

1. A method for reducing gastrointestinal uptake of toxic compounds in a subject having said toxic compounds in the gastrointestinal tract, the method consisting of administering to the subject a composition for reducing the gastrointestinal uptake of toxic compounds, the composition consisting of an effective dose of a *Lactobacillus* and a suitable carrier, wherein the strain of *Lactobacillus* is provided in a viable or non-viable form, wherein the *Lactobacillus* is selected from the group of Lactobacilli consisting of: *Lactobacillus rhamnosus* strain ATCC 27773, *Lactobacillus rhamnosus* strain ATCC 55826, and any combination thereof and wherein the toxic compound is mercury.

2. The method of claim 1, wherein the composition includes approximately $10^9$ of the *Lactobacillus* per ml. or less of the suitable carrier.

3. The method of claim 1, wherein the *Lactobacillus* was cultured in the presence of mercury.

4. The method of claim 1, wherein the carrier is a milk-based product.

5. The method of claim 1, wherein the *Lactobacillus* is *Lactobacillus rhamnosus* strain ATCC 55826.

6. The method of claim 1, wherein the strain of *Lactobacillus* is in the viable form.

7. The method of claim 1, wherein the strain of *Lactobacillus* is in the non-viable form.

8. A method for reducing in a subject gastrointestinal uptake of toxic compounds consumed by the subject through edible or drinkable substances contaminated with the toxic compounds, the method comprising administering to the subject a composition for reducing the gastrointestinal uptake of toxic compounds, the composition comprising an effective dose of a *Lactobacillus* and a suitable carrier, wherein the *Lactobacillus* is provided in a viable or non-viable form, wherein the *Lactobacillus* is selected from the group of Lactobacilli consisting of: *Lactobacillus rhamnosus* strain ATCC 27773, *Lactobacillus rhamnosus* strain ATCC 55826, and any combination thereof, and wherein the toxic compound is mercury.

9. The method of claim 8, wherein the carrier is a milk-based product.

10. The method of claim 8, wherein the composition includes approximately $10^9$ of the *Lactobacillus* per ml. or less of the suitable carrier.

11. The method of claim 8, wherein the *Lactobacillus* is *Lactobacillus rhamnosus* strain ATCC 55826.

12. The method of claim 8, wherein the strain of *Lactobacillus* is in the viable form.

13. The method of claim 8, wherein the strain of *Lactobacillus* is in the non-viable form.

* * * * *